(12) United States Patent
Esteller

(10) Patent No.: US 12,151,108 B2
(45) Date of Patent: Nov. 26, 2024

(54) METHOD AND APPARATUS FOR CLOSED-LOOP STEERING FOR NEUROMODULATION

(71) Applicant: Boston Scientific Neuromodulation Corporation, Valencia, CA (US)

(72) Inventor: Rosana Esteller, Santa Clarita, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 155 days.

(21) Appl. No.: 17/747,774

(22) Filed: May 18, 2022

(65) Prior Publication Data

US 2022/0370808 A1 Nov. 24, 2022

Related U.S. Application Data

(60) Provisional application No. 63/190,442, filed on May 19, 2021.

(51) Int. Cl.
*A61N 1/36* (2006.01)
*A61N 1/05* (2006.01)
(Continued)

(52) U.S. Cl.
CPC .......... *A61N 1/36185* (2013.01); *A61N 1/05* (2013.01); *A61N 1/36071* (2013.01);
(Continued)

(58) Field of Classification Search
CPC .. A61N 1/05; A61N 1/36071; A61N 1/36132; A61N 1/36135; A61N 1/36185; A61N 1/37247; G16H 40/63
See application file for complete search history.

(56) References Cited

U.S. PATENT DOCUMENTS 10,279,182 B2 5/2019 Hou et al.
2012/0277621 A1* 11/2012 Gerber ................... A61B 5/686
600/554

(Continued)

FOREIGN PATENT DOCUMENTS

WO WO-2022245970 A1 11/2022

OTHER PUBLICATIONS

"Automatic Calibration in an Implantable Stimulator Device Having Neural Sensing Capability", U.S. Appl. No. 63/165,825, filed Mar. 25, 2021.

(Continued)

*Primary Examiner* — George Manuel
(74) *Attorney, Agent, or Firm* — Schwegman Lundberg & Woessner, P.A.

(57) ABSTRACT

An example of a neurostimulation system may include a stimulation output circuit to deliver the neurostimulation, a sensing circuit to sense a signal indicative of a response to the neurostimulation, and a stimulation control circuit to control the delivery of the neurostimulation using stimulation parameters. The stimulation control circuit may include a response detector and a steering module. The response detector may be configured to detect signal feature(s) from the sensed signal and to determine a response parameter indicative of an intensity of the response to the neurostimulation using the detected signal feature(s). The steering module may be configured to receive user commands for moving a stimulation field and to adjust the stimulation parameters to move the stimulation field according to the user commands while maintaining a value of the response parameter between thresholds.

20 Claims, 10 Drawing Sheets

(51) Int. Cl.
  *A61N 1/372*    (2006.01)
  *G16H 40/63*    (2018.01)
(52) U.S. Cl.
  CPC ..... *A61N 1/36132* (2013.01); *A61N 1/37247* (2013.01); *G16H 40/63* (2018.01)

(56)           References Cited

U.S. PATENT DOCUMENTS

2014/0135869 A1    5/2014   Carlson et al.
2014/0277282 A1    9/2014   Jaax
2015/0165209 A1*   6/2015   Grandhe ............ A61N 1/37247
                                                       607/59
2015/0217116 A1*   8/2015   Parramon .......... A61N 1/36164
                                                        607/2
2020/0054879 A1    2/2020   Torgerson
2020/0215331 A1    7/2020   Single
2020/0330778 A1    10/2020  Kashyap et al.
2021/0121699 A1    4/2021   Dinsmoor et al.

OTHER PUBLICATIONS

"International Application Serial No. PCT/US2022/029868, International Preliminary Report on Patentability mailed Nov. 30, 2023", 7 pgs.
"International Application Serial No. PCT/US2022/029868, International Search Report mailed Aug. 24, 2022", 4 pgs.
"International Application Serial No. PCT/US2022/029868, Written Opinion mailed Aug. 24, 2022", 5 pgs.

\* cited by examiner

METHOD AND APPARATUS FOR CLOSED-LOOP STEERING FOR NEUROMODULATION

CLAIM OF PRIORITY

This application claims the benefit of priority of U.S. Provisional Patent Application No. 63/190,442, filed May 19, 2021, which is hereby incorporated by reference in its entirety.

TECHNICAL FIELD

This document relates generally to neurostimulation and more particularly to a neurostimulation system that provides for closed-loop steering of stimulation field in stimulation site determination.

BACKGROUND

Neurostimulation, also referred to as neuromodulation, has been proposed as a therapy for a number of conditions. Examples of neurostimulation include Spinal Cord Stimulation (SCS), Deep Brain Stimulation (DBS), Peripheral Nerve Stimulation (PNS), and Functional Electrical Stimulation (FES). Implantable neurostimulation systems have been applied to deliver such a therapy. An implantable neurostimulation system may include an implantable neurostimulator, also referred to as an implantable pulse generator (IPG), and one or more implantable leads each including one or more electrodes. The implantable neurostimulator delivers neurostimulation energy through one or more electrodes placed on or near a target site in the nervous system. An external programming device is used to program the implantable neurostimulator with stimulation parameters controlling the delivery of the neurostimulation energy.

In one example, the neurostimulation energy is delivered to a patient in the form of electrical neurostimulation pulses. The delivery is controlled using stimulation parameters that specify spatial (where to stimulate), temporal (when to stimulate), and informational (patterns of pulses directing the nervous system to respond as desired) aspects of a pattern of neurostimulation pulses. Stimulation parameters specifying the spatial aspects may determine where to place electrodes and/or which electrodes to select for delivering the neurostimulation pulses. This may include searching for an optimal location in or on the patient for delivering the neurostimulation pulses known as the "sweet spot" for a neurostimulation therapy.

SUMMARY

An Example (e.g., "Example 1") of a system for delivering neurostimulation to a patient using one or more electrode arrays including a plurality of contacts is provided. The system may include a stimulation output circuit, a sensing circuit, and a stimulation control circuit. The stimulation output circuit may be configured to deliver the neurostimulation using one or more stimulation contacts selected from the plurality of contacts. The sensing circuit may be configured to sense a signal using one or more sensing contacts selected from the plurality of contacts. The signal is indicative of a response to the neurostimulation. The stimulation control circuit may be configured to control the delivery of the neurostimulation using stimulation parameters. The stimulation control circuit may include a response detector and a steering module. The response detector may be configured to detect one or more signal features from the sensed signal and to determine a response parameter using the detected one or more signal features. The response parameter is indicative of an intensity of the response to the neurostimulation. The steering module may be configured to receive user commands for moving a stimulation field defined by a distribution of a stimulation energy of the neurostimulation over the plurality of contacts and to adjust one or more parameters of the stimulation parameters to move the stimulation field according to the user commands while maintaining a value of the response parameter between an upper threshold and a lower threshold.

In Example 2, the subject matter of Example 1 may optionally be configured such that the sensing circuit is configured to sense a neural signal including evoked potentials, and the response detector is configured to detect one or more evoked potential features from the sensed signal and to determine a response parameter using the detected one or more evoked potential features.

In Example 3, the subject matter of any one or any combination of Examples 1 and 2 may optionally be configured such that the stimulation control circuit further includes a mapping module configured to identify critical stimulation contacts (CSCs) from the plurality of contacts, the CSCs each being a stimulation contact of the stimulation contacts that is associated with overstimulation or understimulation, to identify best sensing contacts (BSCs) from the plurality of contacts for each CSC of the identified CSCs, and to map the identified CSCs to the identified BSCs.

In Example 4, the subject matter of Example 3 may optionally be configured such that the mapping module is configured to execute a mapping algorithm selecting stimulation contacts from the plurality of contacts, selecting sensing contacts from the plurality of contacts for each selected stimulation contact, determining the CSCs from the selected stimulation contacts, and determining the BSCs for each of the CSCs from the selected sensing contacts.

In Example 5, the subject matter of any one or any combination of Examples 3 and 4 may optionally be configured such that the mapping module is configured to map the stimulation parameters associated with each CSC of the identified CSCs to threshold parameters associated with the BSCs identified for that CSC.

In Example 6, the subject matter of any one or any combination of Examples 3 to 5 may optionally be configured such that the steering module is configured to receive the response parameter from the response detector in real time and to adjust the one or more parameters of the stimulation parameters using the received response parameter.

In Example 7, the subject matter of Example 6 may optionally be configured such that the steering module is configured to adjust the one or more parameters of the stimulation parameters to reduce the intensity of stimulation in response to the response parameter exceeding the upper threshold while the stimulation field is moving toward each CSC of the identified CSCs and to adjust the one or more parameters of the stimulation parameters to increase the intensity of stimulation in response to the response parameter falling below the lower threshold while the stimulation field is moving away from each CSC of the identified CSCs.

In Example 8, the subject matter of any one or any combination of Examples 3 to 5 may optionally be configured to further include a storage device storing predetermined values for the response parameter associated with the identified BSCs, and such that the steering module is configured to adjust the one or more parameters of the stimulation parameters using the predetermined values for the response parameter.

In Example 9, the subject matter of any one or any combination of Examples 3 to 8 may optionally be configured such that the steering module is configured to adjust the upper threshold based on a discomfort threshold (DT) of the threshold parameters and to adjust the lower threshold based on a neural threshold (NT) of the threshold parameters. The DT is a value of the response parameter corresponding to a stimulation intensity at which the patient starts to feel discomfort resulting from the neurostimulation. The NT is a minimum value of the response parameter corresponding to a minimum stimulation intensity at which the patient starts to feel the neurostimulation.

In Example 10, the subject matter of Example 9 may optionally be configured such that the steering module is configured to set the upper threshold to aDT and the lower threshold to bNT, and a and b are programmable.

In Example 11, the subject matter of any one or any combination of Examples 9 and 10 may optionally be configured such that the mapping module is configured to determine the NT and the DT.

In Example 12, the subject matter of any one or any combination of Examples 1 to 11 may optionally be configured to further include a user interface including a presentation device and a user input device. The presentation device is configured to display a graphical representation of the one or more electrode arrays and a graphical representation of the stimulation field. The user input device configured to receive the user commands for moving the stimulation field.

In Example 13, the subject matter of Example 12 may optionally be configured such that the user input device is configured to receive the user commands for moving the stimulation field by moving a central point of stimulation (CPS) being a center of the stimulation field, and the presentation device is configured to display the graphical representation of the one or more electrode arrays and the graphical representation of the stimulation field including the CPS.

In Example 14, the subject matter of any one or any combination of Examples 12 and 13 may optionally be configured to include a portable device configured for use by the patient and including the user interface.

In Example 15, the subject matter of Example 14 may optionally be configured such that the portable device includes a smartphone.

An example (e.g., "Example 16") of a method for delivering neurostimulation to a patient is also provided. The method may include delivering the neurostimulation using one or more stimulation contacts selected from a plurality of contacts of one or more electrode arrays, sensing a signal indicative of a response to the neurostimulation using one or more sensing contacts selected from the plurality of contacts, and controlling the delivery of the neurostimulation by adjusting stimulation parameters using a processor. The controlling may include detecting one or more signal features from the sensed signal, determining a response parameter indicative of an intensity of the response to the neurostimulation using the detected one or more signal features, receiving user commands for moving a stimulation field defined by a distribution of a stimulation energy of the neurostimulation over the plurality of contacts, and adjusting one or more parameters of the stimulation parameters to move the stimulation field according to the user commands while maintaining a value of the response parameter between an upper threshold and a lower threshold.

In Example 17, the subject matter of sensing the signal as found in Example 16 may optionally include sensing a neural signal including evoked potentials, and the subject matter of detecting the one or more signal features as found in Example 16 may optionally include detecting one or more evoked potential features from the sensed signal.

In Example 18, the subject matter of any one or any combination of Examples 16 and 17 may optionally further include executing a mapping algorithm using the processor. The executing includes identifying critical stimulation contacts (CSCs) from the plurality of contacts, identifying best sensing contacts (BSCs) from the plurality of contacts for each CSC of the identified CSCs, and mapping the identified CSCs and to the identified BSCs, including mapping the stimulation parameters associated with each CSC of the identified CSCs to threshold parameters associated with the BSCs identified for that CSC. The CSCs are each a stimulation contact of the stimulation contacts that is associated with overstimulation or understimulation, In Example 19, the subject matter of adjusting the one or more parameters of the stimulation parameters as found in Example 18 may optionally include receiving the response parameter in real time, adjusting the one or more parameters of the stimulation parameters to reduce the intensity of stimulation in response to the response parameter received in real time exceeding the upper threshold while the stimulation field is moving toward each CSC of the identified CSCs, and adjusting the one or more parameter of the stimulation parameters to increase the intensity of stimulation in response to the response parameter received in real time falling below the lower threshold while the stimulation field is moving away from the each CSC.

In Example 20, the subject matter of adjusting the one or more parameters of the stimulation parameters as found in Example 18 may optionally include storing predetermined values for the response parameter associated with the identified BSCs, adjusting the one or more parameters of the stimulation parameters to reduce the intensity of stimulation using the predetermined values for the response parameter while the stimulation field is moving toward each CSC of the identified CSCs, and adjusting the one or more parameter of the stimulation parameters to increase the intensity of stimulation using the predetermined values for the response parameter while the stimulation field is moving away from the each CSC.

In Example 21, the subject matter of any one or any combination of Examples 18 to 20 may optionally further include adjusting the upper threshold based on a discomfort threshold (DT) of the threshold parameters and adjusting the lower threshold based on a neural threshold (NT) of the threshold parameters. The DT is a value of the response parameter corresponding to a stimulation intensity at which the patient starts to feel discomfort resulting from the neurostimulation. The NT is a minimum value of the response parameter corresponding to a minimum stimulation intensity at which the patient starts to feel the neurostimulation.

In Example 22, the subject matter of Example 21 may optionally further include receiving programmable values a and b, setting the upper threshold to aDT, and setting the lower threshold to bNT.

In Example 23, the subject matter of any one or any combination of Examples 16 to 22 may optionally further include displaying a graphical representation of the one or more electrode arrays and a graphical representation of the stimulation field on a display screen, receiving the user commands for moving the stimulation field by moving a central point of stimulation (CPS) using a user input device, and graphically showing movement of the stimulation field including the CPS on the display screen as the CPS is being moved. The CPS is a center of the stimulation field;

In Example 24, the subject matter of Example 23 may optionally further include configuring a mobile device for use by the patient to enter the user commands for moving the stimulation field.

An example (e.g., "Example 25") of a non-transitory computer-readable storage medium including instructions, which when executed by a system, cause the system to perform a method for delivering neurostimulation to a patient The method may include delivering the neurostimulation using one or more stimulation contacts selected from a plurality of contacts of one or more electrode arrays, sensing a signal indicative of a response to the neurostimulation using one or more sensing contacts selected from the plurality of contacts, and controlling the delivery of the neurostimulation by adjusting stimulation parameters using a processor. The controlling may include detecting one or more signal features from the sensed signal, determining a response parameter indicative of an intensity of the response to the neurostimulation using the detected one or more signal features, receiving user commands for moving a stimulation field defined by a distribution of a stimulation energy of the neurostimulation over the plurality of contacts, and adjusting one or more parameters of the stimulation parameters to move the stimulation field according to the user commands while maintaining a value of the response parameter between an upper threshold and a lower threshold.

This Summary is an overview of some of the teachings of the present application and not intended to be an exclusive or exhaustive treatment of the present subject matter. Further details about the present subject matter are found in the detailed description and appended claims. Other aspects of the disclosure will be apparent to persons skilled in the art upon reading and understanding the following detailed description and viewing the drawings that form a part thereof, each of which are not to be taken in a limiting sense. The scope of the present disclosure is defined by the appended claims and their legal equivalents.

BRIEF DESCRIPTION OF THE DRAWINGS

The drawings illustrate generally, by way of example, various embodiments discussed in the present document. The drawings are for illustrative purposes only and may not be to scale.

DETAILED DESCRIPTION

Figure 1:
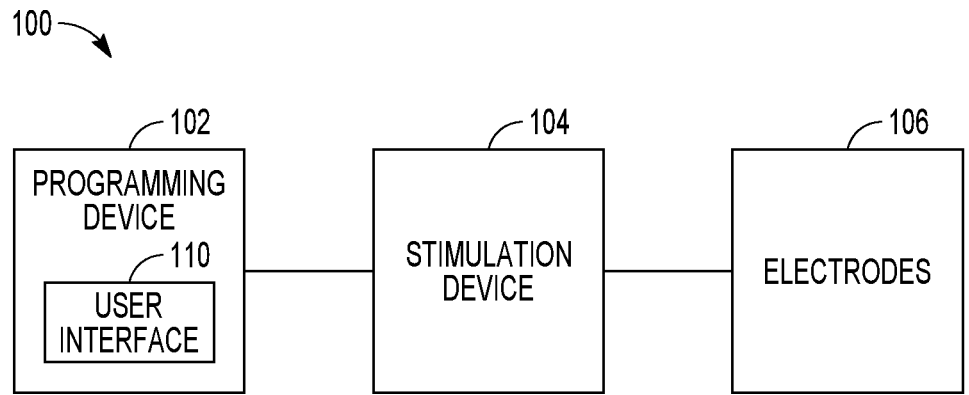
FIG. 1 illustrates an embodiment of a neurostimulation system.

In the following detailed description, reference is made to the accompanying drawings which form a part hereof, and in which is shown by way of illustration specific embodiments in which the invention may be practiced. These embodiments are described in sufficient detail to enable those skilled in the art to practice the invention, and it is to be understood that the embodiments may be combined, or that other embodiments may be utilized, and that structural, logical and electrical changes may be made without departing from the spirit and scope of the present invention. References to "an", "one", or "various" embodiments in this disclosure are not necessarily to the same embodiment, and such references contemplate more than one embodiment. The following detailed description provides examples, and the scope of the present invention is defined by the appended claims and their legal equivalents.

This document discusses, among other things, a neurostimulation system that provides for closed-loop steering of stimulation field in determination of a stimulation site. In various embodiments, the neuromodulation system can include an implantable device configured to deliver neurostimulation (also referred to as neuromodulation) therapies, such as deep brain stimulation (DBS), spinal cord stimulation (SCS), peripheral nerve stimulation (PNS), and vagus nerve stimulation (VNS), and one or more external devices configured to program or adjust the implantable device for its operations and monitor the performance of the implantable device. The closed-loop steering of stimulation field according to the present subject matter can be controlled using such one or more external devices. In this document, unless noted otherwise, a "patient" includes a person receiving treatment delivered from, and/or monitored using, a neurostimulation system according to the present subject matter. A "user" includes a physician, other caregiver who examines and/or treats the patient using the neurostimulation system, or other person who participates in the examination and/or treatment of the patient using the neurostimulation system (e.g., a technically trained representative, a field clinical engineer, a clinical researcher, or a field specialist from the manufacturer of the neurostimulation system).

"Steering" includes controlled movement of a stimulation field or a representation of the stimulation field (e.g., a center of the stimulation field or an electrode at or near the center of the stimulation field). A stimulation field is created when at least one cathode and at least one anode are assigned to any of multiple contacts (also referred to as electrodes, such as contacts in one or more implantable leads and an implantable device of the neurostimulation system). This stimulation field can be spatially moved (i.e., "steered") in any direction where there are contacts available, by changing the cathodes and anodes accordingly. In the case each contact is connected to an independently controllable current source, the field steering can be achieved with high spatial resolution by changing the fractionalization of the cathodes and anodes representing the field to spatially move this stimulation field according to a user-specified direction, as further discussed below in this document.

Therapeutic effectiveness and energy efficiency of a neurostimulation therapy depends on a target location in the patient to which the stimulation is delivered. The optimal target location for a neurostimulation therapy is referred as the "sweet spot" for that neurostimulation therapy. One method for determining the sweet spot includes steering (trolling up and down) the electrode configuration used for delivering the neurostimulation while monitoring the response of the patient until the sweet spot for neurostimulation is found. Such a method is time consuming when performed manually because as the stimulation field is steered up or down, left or right the spinal cord, or in any other direction in any other area (e.g., the brain, peripheral nerves, etc.) of the nervous system, while the other stimulation parameters are constant, the patient needs to be monitored for side effects. For example, for a pain control therapy using neurostimulation, such as SCS, the sweet spot can be considered as the location where pain and paresthesia (stimulation sensation) have the maximum overlap. During the steering for determination of the sweet spot, the intensity of the paresthesia can change from very high (when the patient feels substantial discomfort or zinger) to very low where the paresthesia disappears (when the patient no longer feels the stimulation). This sweet spot search when performed manually takes the user (such as a clinician) much time because besides the anatomical navigation, the user has to constantly adjust the neurostimulation to maintain the intensity of the paresthesia so that during the steering, the patient can always feel the neurostimulation and tells the user whether the stimulation (perceived as the paresthesia) overlaps with the pain while also avoiding side effects.

The present subject matter uses sensed information (rather than the patient's input) to adjust the neurostimulation to maintain the intensity of paresthesia during the steering for locating the sweet spot. A signal indicative of response of the patient to the neurostimulation is sensed, and one or more features indicative of the intensity of paresthesia are detected from the sensed signal. The neurostimulation can be adjusted to substantially maintain the intensity of paresthesia by keeping a parameter measured from the detected features within a specified small range.

For example, in the pain control therapy using SCS, evoked compound action potentials (ECAPs) sensed from the patient include the response of the patient's dorsal columns (axons) being activated by the neurostimulation. The response includes paresthesia as the sensation of stimulation is transmitted to the patient's brain. When this response, which is indicated by the ECAPs, increases, the intensity of the paresthesia also increases. When this response decreases, the intensity of the paresthesia also decreases. Therefore, the ECAPs can be used to indicate the intensity of the paresthesia. The present subject matter measures a parameter (e.g., an amplitude) of a signal feature of a signal including the ECAPs. In one embodiment, the measured parameter is maintained at a substantially constant value for this parameter (e.g., by keeping the value within a specified small range) during the steering for locating the sweet spot by automatically adjusting the intensity of the neurostimulation to minimize changes in the parameter and hence, the intensity of the paresthesia. In another embodiment, the measured parameter is maintained within a range of values defined as acceptable, such that while steering the field during the sweet spot search, the changes in paresthesia intensity are allowed within the permissible range.

The present neurostimulation system includes control of closed-loop steering that uses sensed indication of the patient's paresthesia to automatically adjust stimulation intensity for maintaining the intensity of paresthesia as prescribed. Such a system allows for self-steering in which the patient is the one who drives the search and stops when he or she feels the maximum pain and paresthesia overlap, without causing self-inflicted discomfort, zingers, and/or loss of sensation. This reduces the time for the user to frequently adjust the stimulation intensity while frequently asking the patient, for example, "do you feel better pain-paresthesia overlap here, or here?" This can also reduce effect of the patient's movement, such as coughing, on the result because the patient would know when to pause the steering for the movement.

In various embodiments, the present neurostimulation system can be configured for the patient and/or the user to drive the steering for locating the sweet spot. For example, the closed-loop steering control can be implemented in a programming device as a semi-automatic system used by the user adjusting neurostimulation for the patient. In another example, the closed-loop steering control can be implemented in a device that the patient can use at home, such as in neurostimulation control application installed in a smart phone that allows the patient to move the stimulation field graphically on a touch screen. This allows the patient to adjust the neurostimulation at home, without waiting for an appointment with the user, for example when the patient feels loss of effectiveness in pain control and/or increase of discomfort resulting from the neurostimulation.

FIG. 1 illustrates an embodiment of a neurostimulation system 100. System 100 includes electrodes (also referred to as contacts) 106, a stimulation device 104, and a programming device 102. Electrodes 106 are configured to be placed on or near one or more neural targets in a patient. Stimulation device 104 is configured to be electrically connected to electrodes 106 and deliver neurostimulation energy, such as in the form of electrical pulses, to the one or more neural targets though electrodes 106. The delivery of the neurostimulation is controlled by using a plurality of stimulation parameters, such as stimulation parameters specifying a pattern of the electrical pulses and a selection of electrodes through which each of the electrical pulses is delivered. In various embodiments, at least some parameters of the plurality of stimulation parameters are programmable by a user, such as a physician or other caregiver who treats the patient using system 100. Programming device 102 provides the user with accessibility to the user-programmable parameters. In various embodiments, programming device 102 is configured to be communicatively coupled to stimulation device via a wired or wireless link.

In various embodiments, programming device 102 can include a user interface 110 that allows the user to control the operation of system 100 and monitor the performance of system 100 as well as conditions of the patient including responses to the delivery of the neurostimulation. The user can control the operation of system 100 by setting and/or adjusting values of the user-programmable parameters.

In various embodiments, user interface 110 can include a graphical user interface (GUI) that allows the user to set and/or adjust the values of the user-programmable parameters by creating and/or editing graphical representations of various waveforms. Such waveforms may include, for example, a waveform representing a pattern of neurostimulation pulses to be delivered to the patient as well as individual waveforms that are used as building blocks of the pattern of neurostimulation pulses, such as the waveform of each pulse in the pattern of neurostimulation pulses. The GUI may also allow the user to set and/or adjust stimulation fields each defined by a set of electrodes through which one or more neurostimulation pulses represented by a waveform are delivered to the patient. The stimulation fields may each be further defined by the distribution of the current of each neurostimulation pulse in the waveform. In various embodiments, neurostimulation pulses for a stimulation period (such as the duration of a therapy session) may be delivered to multiple stimulation fields.

In various embodiments, system 100 can be configured for neurostimulation applications. User interface 110 can be configured to allow the user to control the operation of system 100 for neurostimulation. For example, system 100 as well as user interface 110 can be configured for spinal cord stimulation (SCS) applications. Such SCS configuration includes various features that may simplify the task of the user in programming stimulation device 104 for delivering SCS to the patient, such as the features discussed in this document.

Figure 2:
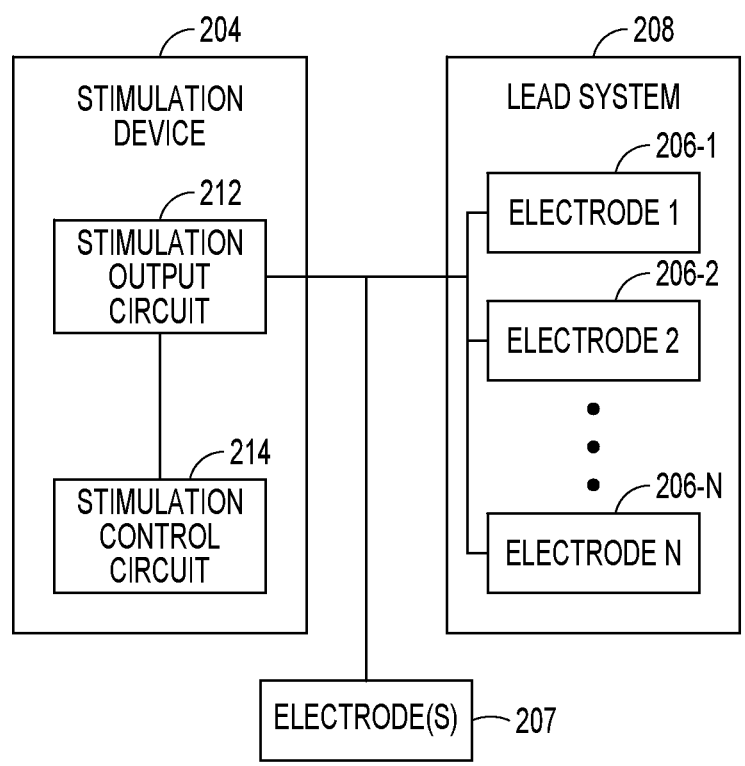
FIG. 2 illustrates an embodiment of a stimulation device and a lead system, such as may be implemented in the neurostimulation system of FIG. 1.

FIG. 2 illustrates an embodiment of a stimulation device 204 and a lead system 208, such as may be implemented in neurostimulation system 100. Stimulation device 204 represents an example of stimulation device 104 and includes a stimulation output circuit 212 and a stimulation control circuit 214. Stimulation output circuit 212 produces and delivers neurostimulation pulses. Stimulation control circuit 214 controls the delivery of the neurostimulation pulses from stimulation output circuit 212 using the plurality of stimulation parameters, which specifies a pattern of the neurostimulation pulses. Lead system 208 includes one or more leads each configured to be electrically connected to stimulation device 204 and a plurality of electrodes 206 (also referred to as an electrode array in this document) distributed in the one or more leads. The plurality of electrodes 206 includes electrode 206-1, electrode 206-2, . . . electrode 206-N, each being a single electrically conductive contact providing for an electrical interface between stimulation output circuit 212 and tissue of the patient (and therefore also referred to as a contact in this document), where N≥2. The neurostimulation pulses are each delivered from stimulation output circuit 212 through a set of electrodes selected from electrodes 206. In various embodiments, the neurostimulation pulses may include one or more individually defined pulses, and the set of electrodes may be individually definable by the user for each of the individually defined pulses or each of collections of pulse intended to be delivered using the same combination of electrodes. In various embodiments, one or more additional electrodes 207 (each of which may be referred to as a reference electrode) can be electrically connected to stimulation device 204, such as one or more electrodes each being a portion of or otherwise incorporated onto a housing of stimulation device 204. Monopolar stimulation uses a monopolar electrode configuration with one or more electrodes selected from electrodes 206 and at least one electrode from electrode(s) 207. Bipolar stimulation uses a bipolar electrode configuration with two electrodes selected from electrodes 206 and none electrode(s) 207. Multipolar stimulation uses a multipolar electrode configuration with multiple (two or more) electrodes selected from electrodes 206 and none of electrode(s) 207.

In various embodiments, the number of leads and the number of electrodes on each lead depend on, for example, the distribution of target(s) of the neurostimulation and the need for controlling the distribution of electric field at each target. In one embodiment, lead system 208 includes 2 leads each having 8 electrodes.

Figure 3:
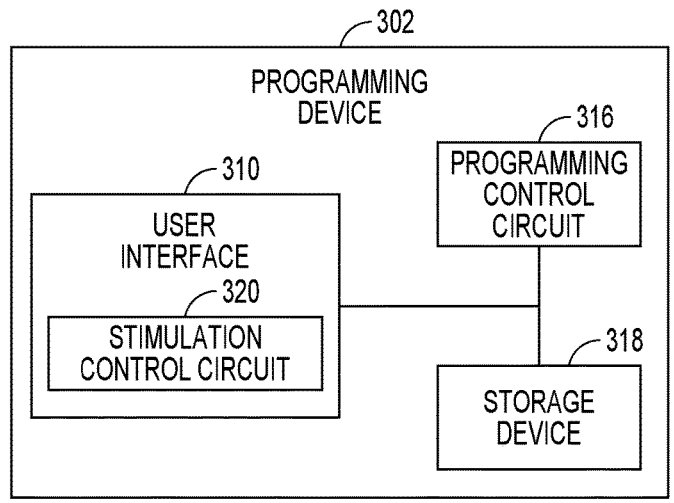
FIG. 3 illustrates an embodiment of a programming device, such as may be implemented in the neurostimulation system of FIG. 1.

FIG. 3 illustrates an embodiment of a programming device 302, such as may be implemented in neurostimulation system 100. Programming device 302 represents an example of programming device 102 and includes a storage device 318, a programming control circuit 316, and a user interface 310. Programming control circuit 316 generates the plurality of stimulation parameters that controls the delivery of the neurostimulation pulses according to a specified neurostimulation program that can define, for example, stimulation waveform and electrode configuration. User interface 310 represents an example of user interface 110 and includes a stimulation control circuit 320. Storage device 318 stores information used by programming control circuit 316 and stimulation control circuit 320, such as information about a stimulation device that relates the neurostimulation program to the plurality of stimulation parameters. In various embodiments, stimulation control circuit 320 can be configured to support one or more functions allowing for programming of stimulation devices, such as stimulation device 104 including its various embodiments as discussed in this document, according to one or more selected neurostimulation programs and/or one or more algorithms for the closed-loop steering as discussed in the document.

In various embodiments, user interface 310 can allow for definition of a pattern of neurostimulation pulses for delivery during a neurostimulation therapy session by creating and/or adjusting one or more stimulation waveforms using a graphical method. The definition can also include definition of one or more stimulation fields each associated with one or more pulses in the pattern of neurostimulation pulses. As used in this document, a "neurostimulation program" can include the pattern of neurostimulation pulses including the one or more stimulation fields, or at least various aspects or parameters of the pattern of neurostimulation pulses including the one or more stimulation fields. In various embodiments, user interface 310 includes a GUI that allows the user to define the pattern of neurostimulation pulses and perform other functions using graphical methods. In this document, "neurostimulation programming" can include the definition of the one or more stimulation waveforms, including the definition of one or more stimulation fields.

In various embodiments, circuits of neurostimulation system 100, including its various embodiments discussed in this document, may be implemented using a combination of hardware and software. For example, the circuit of user interface 110, stimulation control circuit 214, programming control circuit 316, and stimulation control circuit 320, including their various embodiments discussed in this document, can be implemented using an application-specific circuit constructed to perform one or more particular functions and/or a general-purpose circuit programmed to perform such function(s). Such a general-purpose circuit includes, but is not limited to, a microprocessor or a portion thereof, a microcontroller or portions thereof, and a programmable logic circuit or a portion thereof.

Figure 4:
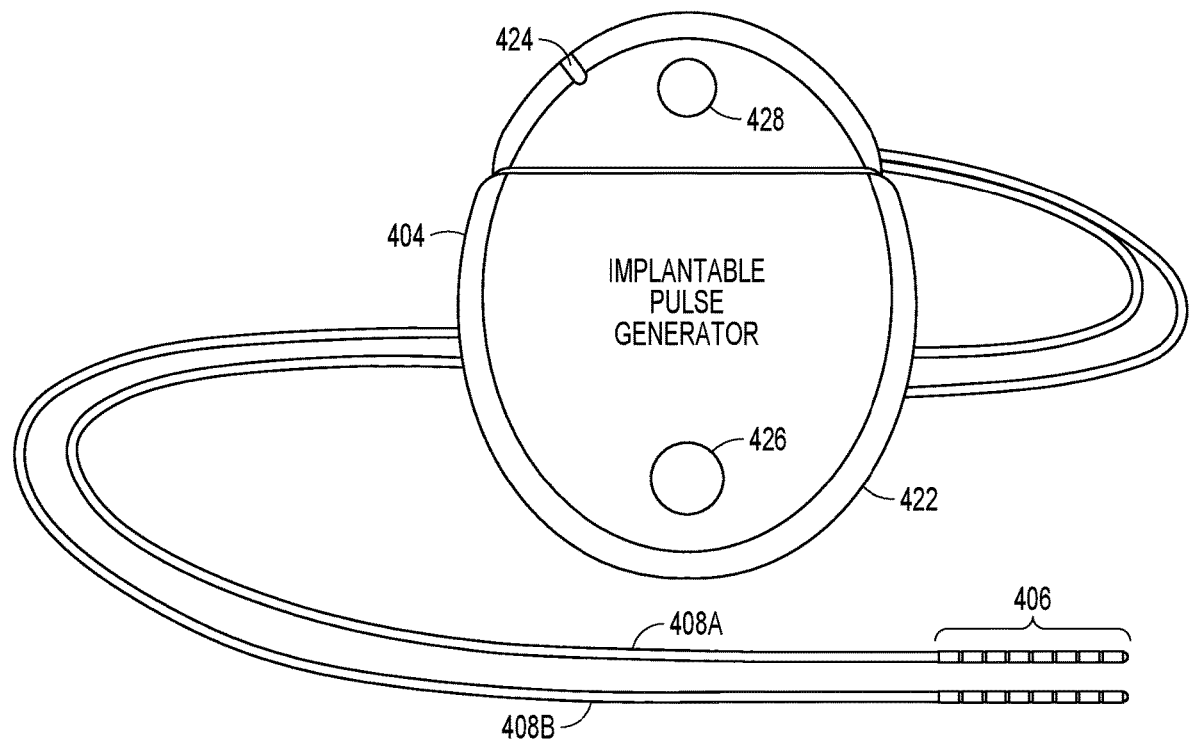
FIG. 4 illustrates an embodiment of an implantable pulse generator (IPG) and an implantable lead system, such as an example implementation of the stimulation device and lead system of FIG. 2.

FIG. 4 illustrates an embodiment of an implantable pulse generator (IPG) 404 and an implantable lead system 408. IPG 404 represents an example implementation of stimulation device 204. Lead system 408 represents an example implementation of lead system 208. As illustrated in FIG. 4, IPG 404 that can be coupled to implantable leads 408A and 408B at a proximal end of each lead. The distal end of each lead includes electrodes (also referred to as contacts) 406 for contacting a tissue site targeted for electrical neurostimulation. As illustrated in FIG. 4, leads 408A and 408B each include 8 electrodes 406 at the distal end. The number and arrangement of leads 408A and 408B and electrodes 406 as shown in FIG. 4 are only an example, and other numbers and arrangements are possible. In various embodiments, the electrodes are ring electrodes. In various embodiments applying DBS or SCS, the implantable leads and electrodes may be configured by shape and size to provide electrical neurostimulation energy to a neuronal target included in the patient's brain or configured to provide electrical neurostimulation energy to target nerve cells in the patient's spinal cord.

Figure 5:
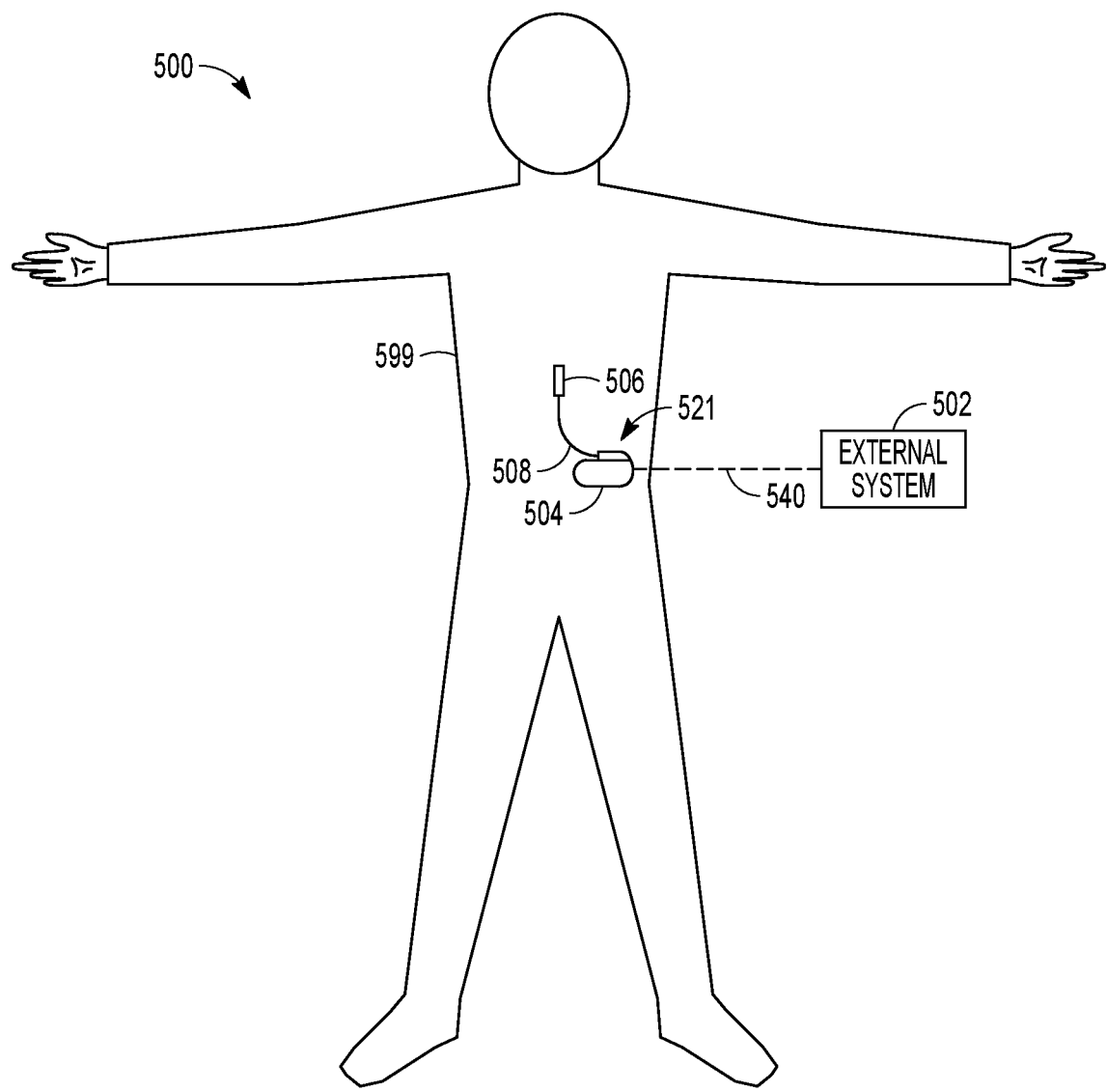
FIG. 5 illustrates an embodiment of an IPG and an implantable lead system, such as the IPG and lead system of FIG. 4, arranged to provide neurostimulation to a patient.

FIG. 5 illustrates an implantable neurostimulation system 500 and portions of an environment in which system 500 may be used. System 500 includes an implantable system 521, an external system 502, and a telemetry link 540 providing for wireless communication between implantable system 521 and external system 502. Implantable system 521 is illustrated in FIG. 5 as being implanted in the patient's body 599.

Implantable system 521 includes an implantable stimulator (also referred to as an implantable pulse generator, or IPG) 504, a lead system 508, and electrodes (also referred to as contacts) 506, which represent an example of stimulation device 204, lead system 208, and electrodes 206, respectively. External system 502 represents an example of programming device 302. In various embodiments, external system 502 includes one or more external (non-implantable) devices each allowing the user and/or the patient to communicate with implantable system 521. In some embodiments, external 502 includes a programming device intended for the user to initialize and adjust settings for implantable stimulator 504 and a remote control device intended for use by the patient. For example, the remote control device may allow the patient to turn implantable stimulator 504 on and off and/or adjust certain patient-programmable parameters of the plurality of stimulation parameters.

The sizes and shapes of the elements of implantable system 521 and their location in body 599 are illustrated by way of example and not by way of restriction. An implantable system is discussed as a specific application of the programming according to various embodiments of the present subject matter. In various embodiments, the present subject matter may be applied in programming any type of stimulation device that uses electrical pulses as stimuli, regarding less of stimulation targets in the patient's body and whether the stimulation device is implantable.

Returning to FIG. 4, the IPG 404 can include a hermetically-sealed IPG case 422 to house the electronic circuitry of IPG 404. IPG 404 can include an electrode 426 formed on IPG case 422. IPG 404 can include an IPG header 424 for coupling the proximal ends of leads 408A and 408B. IPG header 424 may optionally also include an electrode 428. Electrodes 426 and/or 428 represent embodiments of electrode(s) 207 and may each be referred to as a reference electrode. Neurostimulation energy can be delivered in a monopolar (also referred to as unipolar) mode using electrode 426 or electrode 428 and one or more electrodes selected from electrodes 406. Neurostimulation energy can be delivered in a bipolar mode using a pair of electrodes of the same lead (lead 408A or lead 408B). Neurostimulation energy can be delivered in an extended bipolar mode using one or more electrodes of a lead (e.g., one or more electrodes of lead 408A) and one or more electrodes of a different lead (e.g., one or more electrodes of lead 408B).

The electronic circuitry of IPG 404 can include a control circuit that controls delivery of the neurostimulation energy. The control circuit can include a microprocessor, a digital signal processor, application specific integrated circuit (ASIC), or other type of processor, interpreting or executing instructions included in software or firmware. The neurostimulation energy can be delivered according to specified (e.g., programmed) modulation parameters. Examples of setting modulation parameters can include, among other things, selecting the electrodes or electrode combinations used in the stimulation, configuring an electrode or electrodes as the anode or the cathode for the stimulation, specifying the percentage of the neurostimulation provided by an electrode or electrode combination, and specifying stimulation pulse parameters. Examples of pulse parameters include, among other things, the amplitude of a pulse (specified in current or voltage), pulse duration (e.g., in microseconds), pulse rate (e.g., in pulses per second), and parameters associated with a pulse train or pattern such as burst rate (e.g., an "on" modulation time followed by an "off" modulation time), amplitudes of pulses in the pulse train, polarity of the pulses, etc.

Figure 6:
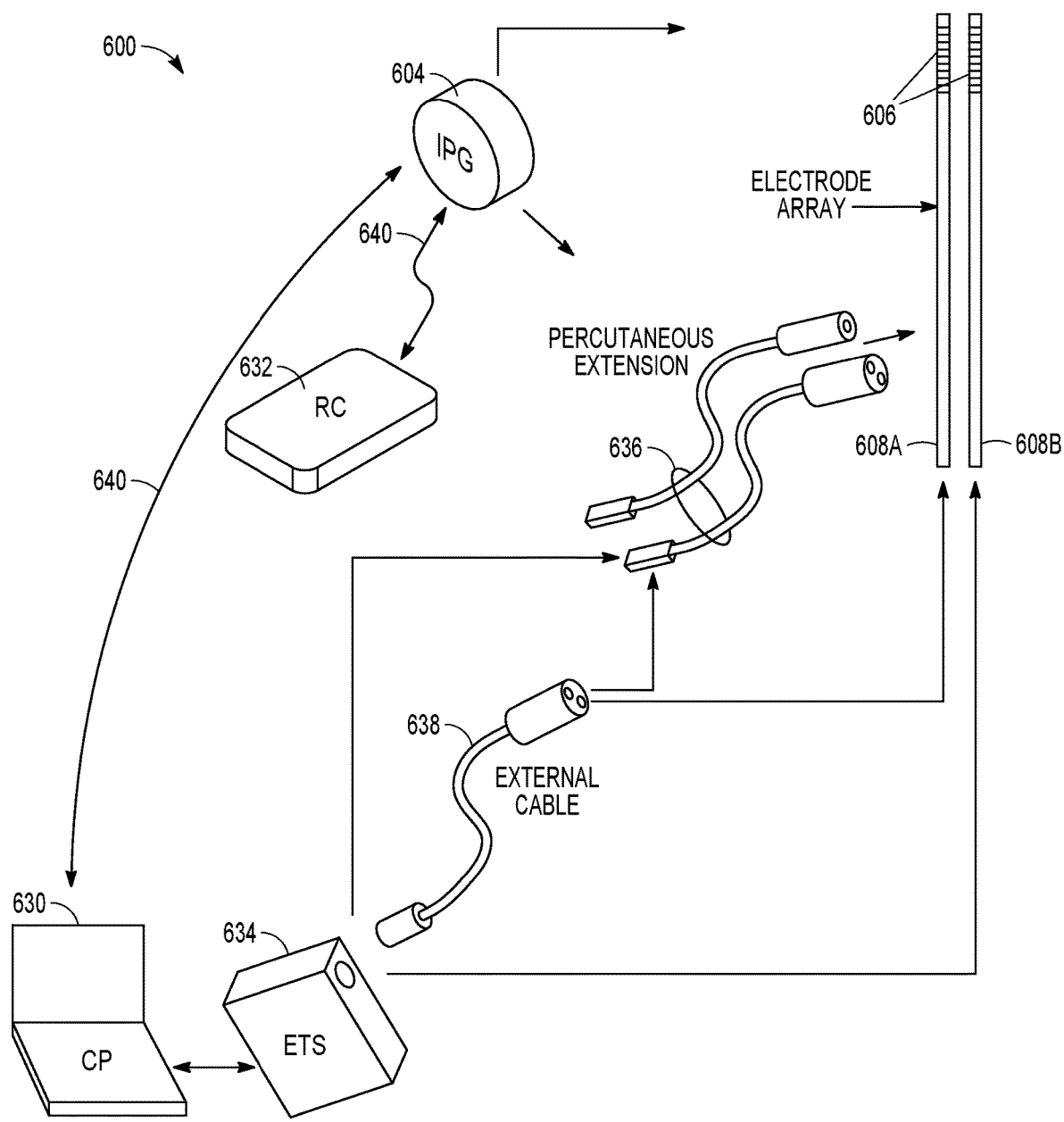
FIG. 6 illustrates an embodiment of portions of a neurostimulation system.

FIG. 6 illustrates an embodiment of portions of a neurostimulation system 600. System 600 includes an IPG 604, implantable neurostimulation leads 608A and 608B, an external remote controller (RC) 632, a clinician's programmer (CP) 630, and an external trial stimulator (ETS, also referred to as external trial modulator, ETM) 634, IPG 604 may be electrically coupled to leads 608A and 608B directly or through percutaneous extension leads 636. ETS 634 may be electrically connectable to leads 608A and 608B via one or both of percutaneous extension leads 636 and/or external cable 638. System 600 represents an example of system 100, with IPG 604 representing an embodiment of stimulation device 104, electrodes (also referred to as contacts) 606 of leads 608A and 608B representing electrodes 106, and CP 630, RC 632, and ETS 634 collectively representing programming device 102.

ETS 634 may be standalone or incorporated into CP 630. ETS 634 may have similar pulse generation circuitry as IPG 604 to deliver neurostimulation energy according to specified modulation parameters as discussed above. ETS 634 is an external device that is typically used as a preliminary stimulator after leads 408A and 408B have been implanted and used prior to stimulation with IPG 604 to test the patient's responsiveness to the stimulation that is to be provided by IPG 604. Because ETS 634 is external it may be more easily configurable than IPG 604.

CP 630 can configure the neurostimulation provided by ETS 634. If ETS 634 is not integrated into CP 630, CP 630 may communicate with ETS 634 using a wired connection (e.g., over a USB link) or by wireless telemetry using a wireless communications link 640. CP 630 also communicates with IPG 604 using a wireless communications link 640.

An example of wireless telemetry is based on inductive coupling between two closely-placed coils using the mutual inductance between these coils. This type of telemetry is referred to as inductive telemetry or near-field telemetry because the coils must typically be closely situated for obtaining inductively coupled communication. IPG 604 can include the first coil and a communication circuit. CP 630 can include or otherwise electrically connected to the second coil such as in the form of a wand that can be place near IPG 604. Another example of wireless telemetry includes a far-field telemetry link, also referred to as a radio frequency (RF) telemetry link. A far-field, also referred to as the Fraunhofer zone, refers to the zone in which a component of an electromagnetic field produced by the transmitting electromagnetic radiation source decays substantially proportionally to 1/r, where r is the distance between an observation point and the radiation source. Accordingly, far-field refers to the zone outside the boundary of $r=\lambda/2\pi$, where $\lambda$ is the wavelength of the transmitted electromagnetic energy. In one example, a communication range of an RF telemetry link is at least six feet but can be as long as allowed by the particular communication technology. RF antennas can be included, for example, in the header of IPG 604 and in the housing of CP 630, eliminating the need for a wand or other means of inductive coupling. An example is such an RF telemetry link is a Bluetooth® wireless link.

CP 630 can be used to set modulation parameters for the neurostimulation after IPG 604 has been implanted. This allows the neurostimulation to be tuned if the requirements for the neurostimulation change after implantation. CP 630 can also upload information from IPG 604.

RC 632 also communicates with IPG 604 using a wireless link 640. RC 632 may be a communication device used by the user or given to the patient. RC 632 may have reduced programming capability compared to CP 630. This allows the user or patient to alter the neurostimulation therapy but does not allow the patient full control over the therapy. For example, the patient may be able to increase the amplitude of neurostimulation pulses or change the time that a preprogrammed stimulation pulse train is applied. RC 632 may be programmed by CP 630. CP 630 may communicate with the RC 632 using a wired or wireless communications link. In some embodiments, CP 630 can program RC 632 when remotely located from RC 632. In various embodiments, RC 632 can be a dedicated device or a general-purpose device configured to perform the functions of RC 632, such as a smartphone, a tablet computer, or other smart/mobile device.

Figure 7:
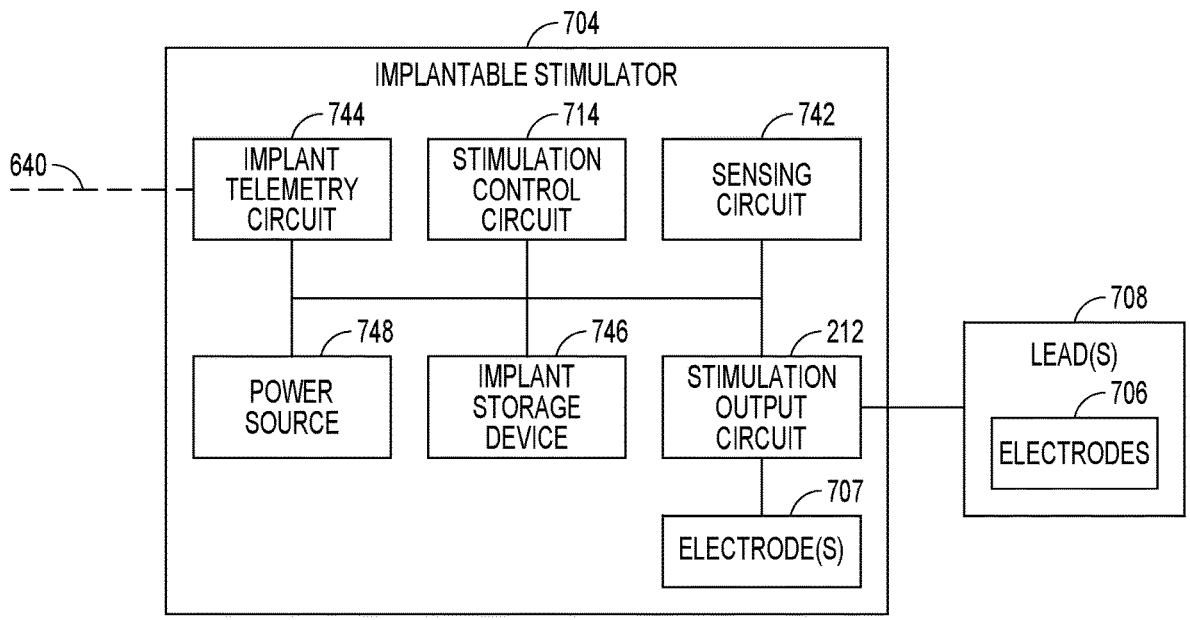
FIG. 7 illustrates an embodiment of an implantable stimulator and one or more leads of an implantable neurostimulation system, such as the implantable neurostimulation system of FIG. 6.

FIG. 7 illustrates an embodiment of implantable stimulator 704 and one or more leads 708 of an implantable neurostimulation system, such as implantable system 600. Implantable stimulator 704 represents an example of stimulation device 104 or 204 and may be implemented, for example, as IPG 604. Lead(s) 708 represents an example of lead system 208 and may be implemented, for example, as implantable leads 608A and 608B. Lead(s) 708 includes electrodes (also referred to as contacts) 706, which represents an example of electrodes 106 or 206 and may be implemented as electrodes 606.

Implantable stimulator 704 may include a sensing circuit 742 that provides the stimulator with a sensing capability, stimulation output circuit 212, a stimulation control circuit 714, an implant storage device 746, an implant telemetry circuit 744, a power source 748, and one or more electrodes 707. Sensing circuit 742 can one or more physiological signals for purposes of patient monitoring and/or feedback control of the neurostimulation. In various embodiments, sensing circuit 742 can sense one or more ESG signals using electrodes placed over or under the dura of the spinal cord, such as electrodes 706 (which can include epidural and/or intradural electrodes). In addition to one or more ESG signals, examples of the one or more physiological signals include neural and other signals each indicative of a condition of the patient that is treated by the neurostimulation and/or a response of the patient to the delivery of the neurostimulation. Stimulation output circuit 212 is electrically connected to electrodes 706 through one or more leads 708 as well as electrodes 707 and delivers each of the neurostimulation pulses through a set of electrodes selected from electrodes 706 and electrode(s) 707. Stimulation control circuit 714 represents an example of stimulation control circuit 214 and controls the delivery of the neurostimulation pulses using the plurality of stimulation parameters specifying the pattern of neurostimulation pulses. In one embodiment, stimulation control circuit 714 controls the delivery of the neurostimulation pulses using the one or more sensed physiological signals. Implant telemetry circuit 744 provides implantable stimulator 704 with wireless communication with another device such as CP 630 and RC 632, including receiving values of the plurality of stimulation parameters from the other device. Implant storage device 746 can store one or more neurostimulation programs and values of the plurality of stimulation parameters for each of the one or more neurostimulation programs. Power source 748 provides implantable stimulator 704 with energy for its operation. In one embodiment, power source 748 includes a battery. In one embodiment, power source 748 includes a rechargeable battery and a battery charging circuit for charging the rechargeable battery. Implant telemetry circuit 744 may also function as a power receiver that receives power transmitted from an external device through an inductive couple. Electrode(s) 707 allow for delivery of the neurostimulation pulses in the monopolar mode. Examples of electrode(s) 707 include electrode 426 and electrode 418 in IPG 404 as illustrated in FIG. 4.

In one embodiment, implantable stimulator 704 is used as a master database. A patient implanted with implantable stimulator 704 (such as may be implemented as IPG 604) may therefore carry patient information needed for his or her medical care when such information is otherwise unavailable. Implant storage device 746 is configured to store such patient information. For example, the patient may be given a new RC 632 (e.g., by installing a new application in a smart device such as a smartphone) and/or travel to a new clinic where a new CP 630 is used to communicate with the device implanted in him or her. The new RC 632 and/or CP 630 can communicate with implantable stimulator 704 to retrieve the patient information stored in implant storage device 746 through implant telemetry circuit 744 and wireless communication link 640 and allow for any necessary adjustment of the operation of implantable stimulator 704 based on the retrieved patient information. In various embodiments, the patient information to be stored in implant storage device 746 may include, for example, positions of lead(s) 708 and electrodes 706 relative to the patient's anatomy (transformation for fusing computerized tomogram (CT) of post-operative lead placement to magnetic resonance imaging (MRI) of the brain), clinical effect map data, objective measurements using quantitative assessments of symptoms (for example using micro-electrode recording, accelerometers, and/or other sensors), and/or any other information considered important or useful for providing adequate care for the patient. In various embodiments, the patient information to be stored in implant storage device 746 may include data transmitted to implantable stimulator 704 for storage as part of the patient information and data acquired by implantable stimulator 704, such as by using sensing circuit 742.

In various embodiments, sensing circuit 742 (if included), stimulation output circuit 212, stimulation control circuit 714, implant telemetry circuit 744, implant storage device 746, and power source 748 are encapsulated in a hermetically sealed implantable housing or case, and electrode(s) 707 are formed or otherwise incorporated onto the case. In various embodiments, lead(s) 708 are implanted such that electrodes 706 are placed on and/or around one or more targets to which the neurostimulation pulses are to be delivered, while implantable stimulator 704 is subcutaneously implanted and connected to lead(s) 708 at the time of implantation.

Figure 8:
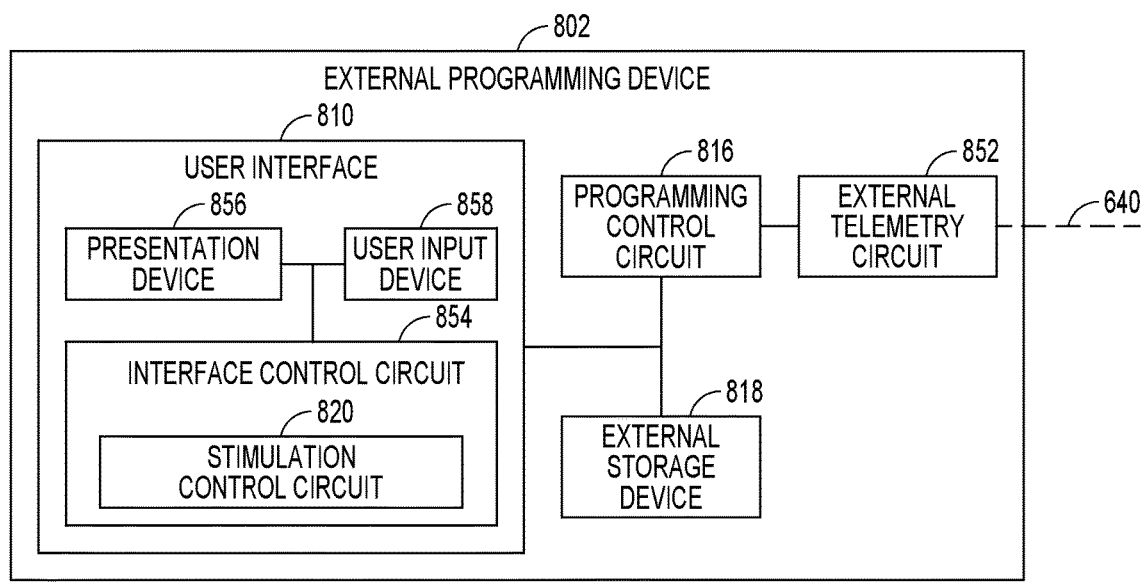
FIG. 8 illustrates an embodiment of an external programming device of an implantable neurostimulation system, such as the implantable neurostimulation system of FIG. 6.

FIG. 8 illustrates an embodiment of an external programming device 802 of an implantable neurostimulation system, such as system 600. External programming device 802 represents an example of programming device 102 or 302, and may be implemented, for example, as CP 630 and/or RC 632. External programming device 802 includes an external telemetry circuit 852, an external storage device 818, a programming control circuit 816, and a user interface 810.

External telemetry circuit 852 provides external programming device 802 with wireless communication with another device such as implantable stimulator 704 via wireless communication link 640, including transmitting the plurality of stimulation parameters to implantable stimulator 704 and receiving information including the patient data from implantable stimulator 704. In one embodiment, external telemetry circuit 852 also transmits power to implantable stimulator 704 through an inductive couple.

In various embodiments, wireless communication link 640 can include an inductive telemetry link (near-field telemetry link) and/or a far-field telemetry link (RF telemetry link). This can allow for patient mobility during programming and assessment when needed. For example, wireless communication link 640 can include at least a far-field telemetry link that allows for communications between external programming device 802 and implantable stimulator 704 over a relative long distance, such as up to about 20 meters. External telemetry circuit 852 and implant telemetry circuit 744 each include an antenna and RF circuitry configured to support such wireless telemetry.

External storage device 818 stores one or more stimulation waveforms for delivery during a neurostimulation therapy session, such as a DBS or SCS therapy session, as well as various parameters and building blocks for defining one or more waveforms. The one or more stimulation waveforms may each be associated with one or more stimulation fields and represent a pattern of neurostimulation pulses to be delivered to the one or more stimulation field during the neurostimulation therapy session. In various embodiments, each of the one or more stimulation waveforms can be selected for modification by the user and/or for use in programming a stimulation device such as implantable stimulator 704 to deliver a therapy. In various embodiments, each waveform in the one or more stimulation waveforms is definable on a pulse-by-pulse basis, and external storage device 818 may include a pulse library that stores one or more individually definable pulse waveforms each defining a pulse type of one or more pulse types. External storage device 818 also stores one or more individually definable stimulation fields. Each waveform in the one or more stimulation waveforms is associated with at least one field of the one or more individually definable stimulation fields. Each field of the one or more individually definable stimulation fields is defined by a set of electrodes through a neurostimulation pulse is delivered. In various embodiments, each field of the one or more individually definable fields is defined by the set of electrodes through which the neurostimulation pulse is delivered and a current distribution of the neurostimulation pulse over the set of electrodes. In one embodiment, the current distribution is defined by assigning a fraction of an overall pulse amplitude to each electrode of the set of electrodes. Such definition of the current distribution may be referred to as "fractionalization" in this document. In another embodiment, the current distribution is defined by assigning an amplitude value to each electrode of the set of electrodes. For example, the set of electrodes may include 2 electrodes used as the anode and an electrode as the cathode for delivering a neurostimulation pulse having a pulse amplitude of 4 mA. The current distribution over the 2 electrodes used as the anode needs to be defined. In one embodiment, a percentage of the pulse amplitude is assigned to each of the 2 electrodes, such as 75% assigned to electrode 1 and 25% to electrode 2. In another embodiment, an amplitude value is assigned to each of the 2 electrodes, such as 3 mA assigned to electrode 1 and 1 mA to electrode 2. Control of the current in terms of percentages allows precise and consistent distribution of the current between electrodes even as the pulse amplitude is adjusted. It is suited for thinking about the problem as steering a stimulation locus, and stimulation changes on multiple contacts simultaneously to move the locus while holding the stimulation amount constant. Control and displaying the total current through each electrode in terms of absolute values (e.g., mA) allows precise dosing of current through each specific electrode. It is suited for changing the current one contact at a time (and allows the user to do so) to shape the stimulation like a piece of clay (pushing/pulling one spot at a time).

Programming control circuit 816 represents an example of programming control circuit 316 and generates the plurality of stimulation parameters, which is to be transmitted to implantable stimulator 704, based on a specified neurostimulation program (e.g., the pattern of neurostimulation pulses as represented by one or more stimulation waveforms and one or more stimulation fields, or at least certain aspects of the pattern). The neurostimulation program may be created and/or adjusted by the user using user interface 810 and stored in external storage device 818. In various embodiments, programming control circuit 816 can check values of the plurality of stimulation parameters against safety rules to limit these values within constraints of the safety rules. In one embodiment, the safety rules are heuristic rules.

User interface 810 represents an example of user interface 310 and allows the user to define the pattern of neurostimulation pulses and perform various other monitoring and programming tasks. User interface 810 includes a display screen 856, a user input device 858, and an interface control circuit 854. Display screen 856 may include any type of interactive or non-interactive screens, and user input device 858 may include any type of user input devices that supports the various functions discussed in this document, such as touchscreen, keyboard, keypad, touchpad, trackball, joystick, and mouse. In one embodiment, user interface 810 includes a GUI. The GUI may also allow the user to perform any functions discussed in this document where graphical presentation and/or editing are suitable as may be appreciated by those skilled in the art.

Interface control circuit 854 controls the operation of user interface 810 including responding to various inputs received by user input device 858 and defining the one or more stimulation waveforms. Interface control circuit 854 includes a stimulation control circuit 820.

In various embodiments, external programming device 802 can have operation modes including a composition mode and a real-time programming mode. Under the composition mode (also known as the pulse pattern composition mode), user interface 810 is activated, while programming control circuit 816 is inactivated. Programming control circuit 816 does not dynamically updates values of the plurality of stimulation parameters in response to any change in the one or more stimulation waveforms. Under the real-time programming mode, both user interface 810 and programming control circuit 816 are activated. Programming control circuit 816 dynamically updates values of the plurality of stimulation parameters in response to changes in the set of one or more stimulation waveforms and transmits the plurality of stimulation parameters with the updated values to implantable stimulator 704.

Stimulation control circuit 820 represents an example of stimulation control circuit 320 and can be configured to provide for closed-loop control of steering of stimulation field according to the present subject matter. In various embodiments, User interface 810 can be configured to allow the user and/or the patient to drive the steering, with stimulation control circuit 820 adjusting the stimulation parameters for substantially maintaining a level of paresthesia while the stimulation field is being moved.

Figure 9:
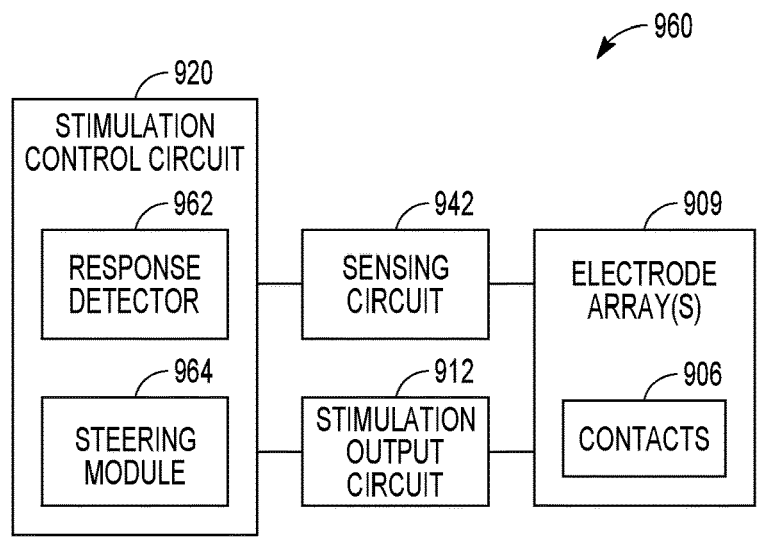
FIG. 9 illustrates an embodiment of a system for closed-loop steering of a stimulation field, such as may be implemented in the neurostimulation system of FIG. 1.

FIG. 9 illustrates an embodiment of a system 960 for closed-loop steering of a stimulation field. System 960 includes one or more electrode arrays 909 including a plurality of contacts (as referred to as electrodes) 906, a stimulation output circuit 912, a sensing circuit 942, and a stimulation control circuit 920. Stimulation output circuit 912 can deliver neurostimulation to a patient using one or more stimulation contacts selected from contacts 906. Sensing circuit 942 can sense a signal from the patient using one or more sensing contacts selected from contacts 906. The sensed signal is indicative of a response of the patient to the neurostimulation. Stimulation control circuit 902 can control the delivery of the neurostimulation using stimulation parameters and can include a response detector 962 and a steering module 964. Response detector 962 can detect one or more signal features from the sensed signal and determine a response parameter using the detected one or more signal features. The response parameter is indicative of an intensity of the response of the patient to the neurostimulation. Steering module 964 can receive user commands for moving a stimulation field and adjust one or more parameters of the stimulation parameters to move the stimulation field according to the user commands while maintaining a value of the response parameter between an upper threshold and a lower threshold. The stimulation field is defined by stimulation parameters controlling a distribution of a stimulation energy of the neurostimulation over the plurality of contacts System 960 can be implemented in neurostimulation systems such as systems 100, 500, and 600. In various embodiments, system 960 can be implemented in an implantable medical device, such as IPG 404, IPG or implantable stimulator 504, IPG 604, or implantable stimulator 704, and an external programming device, such as external system 502, CP 630, RC 632, or external programming device 802, as discussed in this document. For example, when system 960 is implemented in implantable stimulator 704 and external programming device 802, lead(s) 708 can include electrode array(s) 909 including contacts 906, stimulation output circuit 212 can be configured to include stimulation output circuit 912, sensing circuit 742 can be configured to include sensing circuit 942, and stimulation control circuit 714 and/or stimulation control circuit 820 can be configured to include stimulation control circuit 920. In various other embodiments, system 960 can be implemented in a single implantable or non-implantable neurostimulator.

Figure 10:
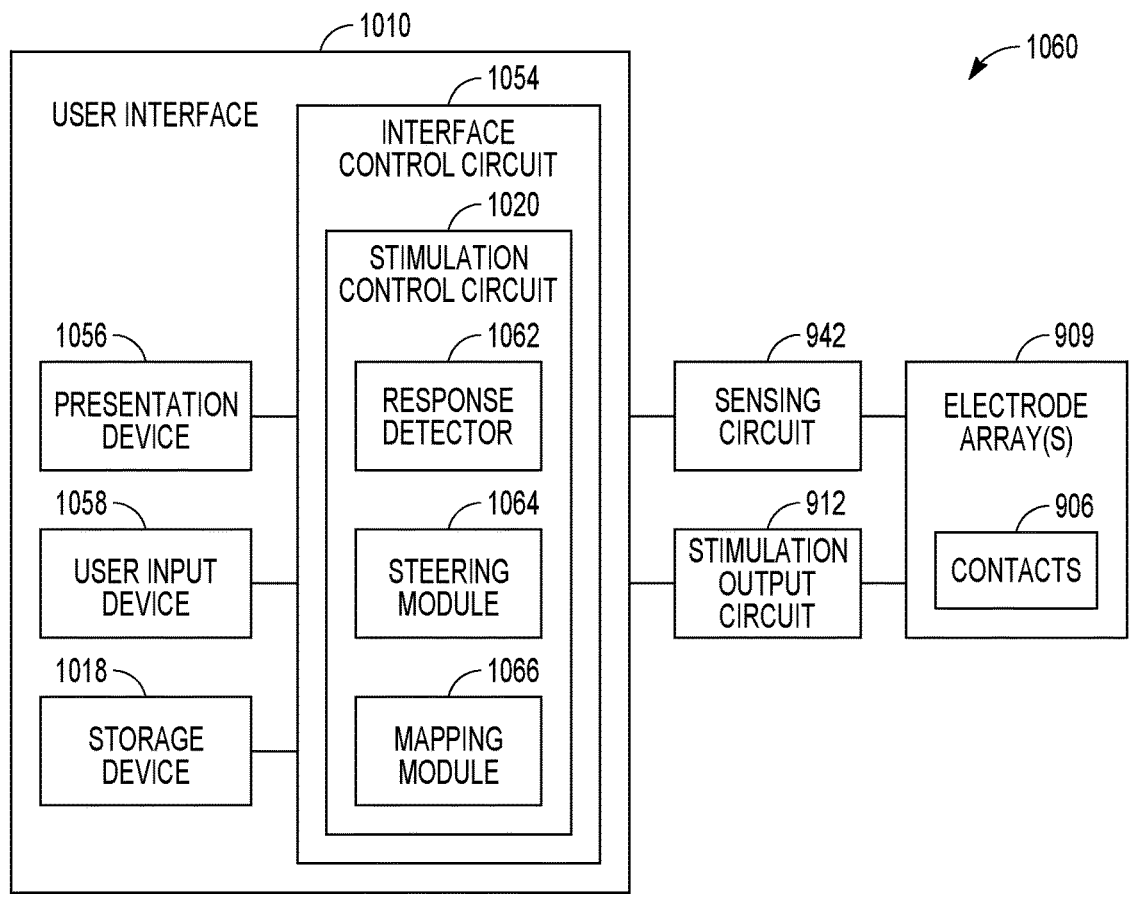
FIG. 10 illustrates an embodiment of another system for closed-loop steering of a stimulation field, such as a further embodiment of the system of FIG. 9 and may be implemented in the neurostimulation system of FIG. 1.
Figure 11:
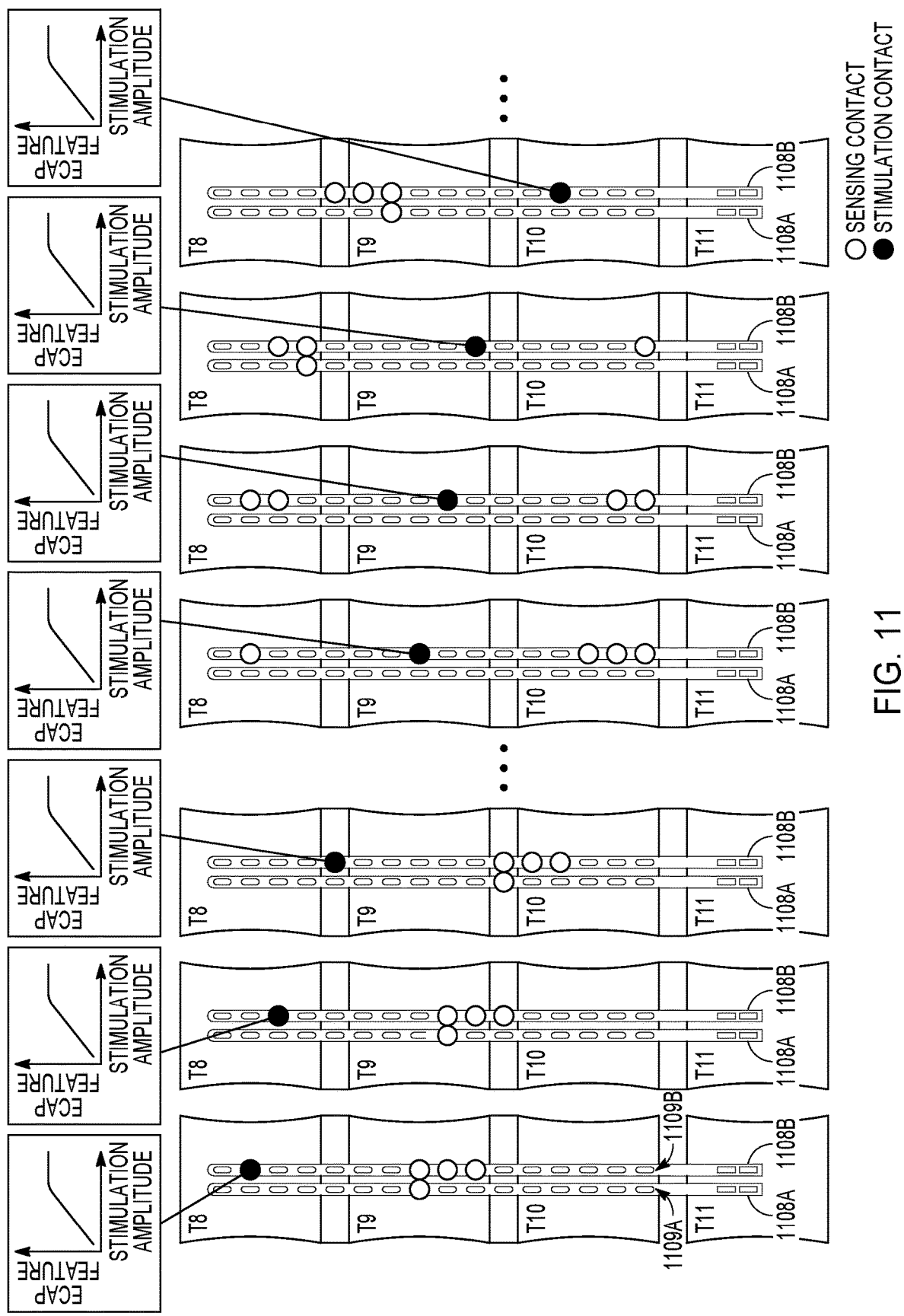
FIG. 11 illustrates an embodiment of a portion of a process for mapping critical stimulation contacts (CSCs) to best sensing contacts (BSCs) and steering the stimulation field while maintain a response intensity.
Figure 12:
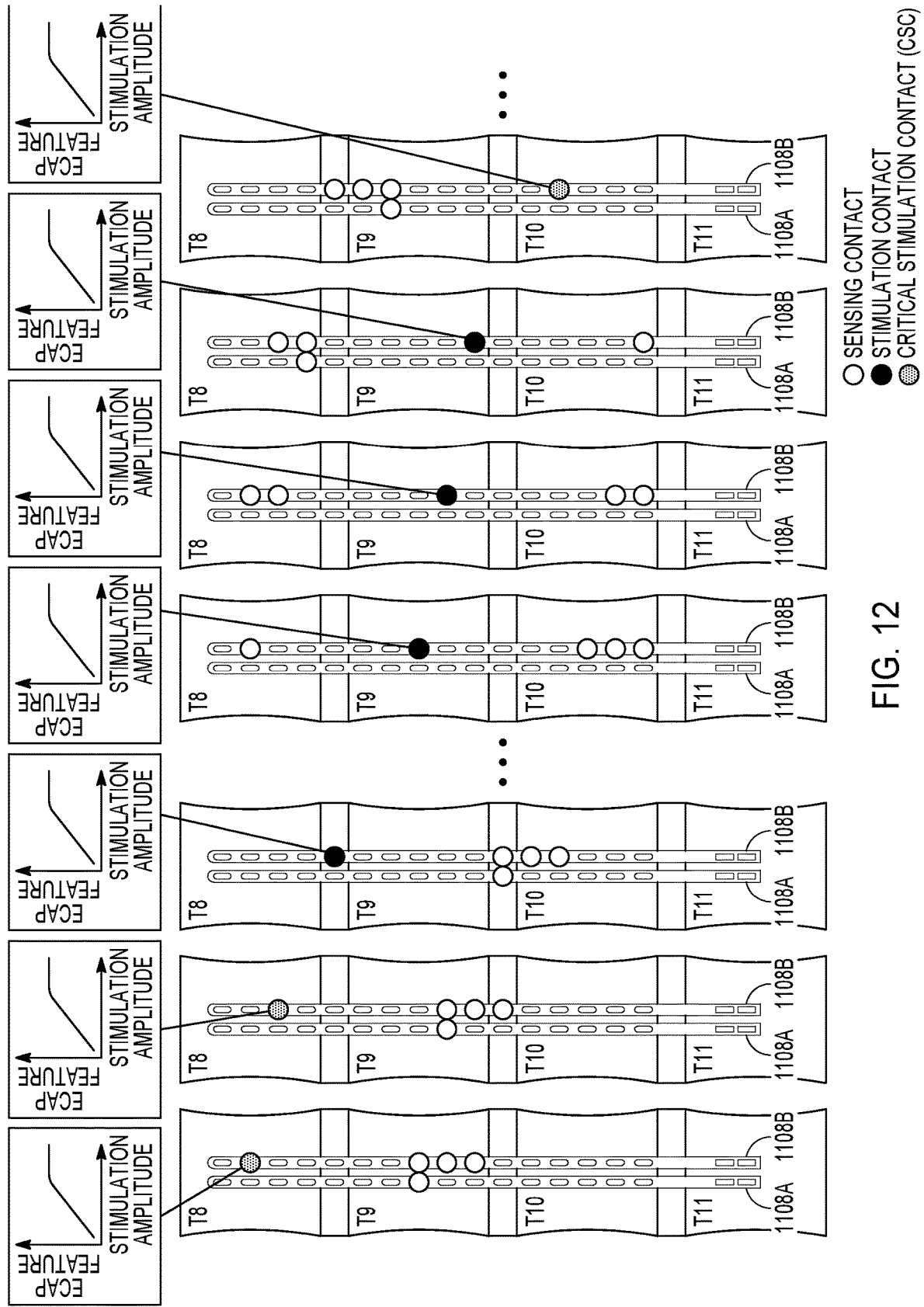
FIG. 12 illustrates an embodiment of another portion of the process of FIG. 11.

FIG. 10 illustrates an embodiment of a system 1060 for closed-loop steering of a stimulation field. System 1060 can represent an example of system 960 and includes electrode array(s) 909 including contact(s) 906, stimulation output circuit 912, sensing circuit 942, and a user interface 1010. In an example as illustrated in FIGS. 11 and 12, electrode arrays 909 can be implemented as electrodes arrays 1109A and 1109B of leads 1108A and 1108B, respectively, and electrodes arrays 1109A and 1109B each include 16 contacts. In other examples, electrode array(s) 909 can each include 16 or 32 contacts of a paddle lead or 8 contacts or a cylindrical lead.

Stimulation output circuit 912 can deliver the neurostimulation using one or more stimulation contacts selected from contacts 906. Assignment of the one or more stimulation contacts (e.g., cathodic and anodic fractionalizations assigned to contacts 906) can be changed to steer the stimulation field for searching the sweet spot. After contacts 906 are placed in or on the patient for a neurostimulation therapy, critical stimulation contacts (CSCs) can be identified from contacts 906 for producing the most significant evoked response when being used to deliver the neurostimulation. CSCs are each a stimulation contact associated with overstimulation (stimulation that causes discomfort of the patient) or understimulation (stimulation that is not felt by the patient). In various embodiments, CSCs can be identified as producing either: (1) a large evoked response or a large increase in the evoked response when the stimulation field is moving (e.g., when a detected response intensity exceeds a specified high threshold or when a detected increase in the response intensity exceeds a specified change threshold), or (2) a small evoked response or a large decrease in the evoked response when the stimulation field is moving (e.g., when a detected response intensity falls below a specified low threshold or when a detected decrease in the response intensity exceeds the specified change threshold).

Sensing circuit 942 can sense a signal indicative of a response to the neurostimulation using one or more sensing contacts selected from contacts 906. For each CSC identified, best sensing contacts (BSCs) for that CSC can be identified from contacts 906 as sensing contacts providing for best sensing of the response to the neurostimulation when delivered to that CSC (e.g., a specified number of sensing contacts with which the highest response intensity is seen).

User interface 1010 can include a presentation device 1056, a user input device 1058, a storage device 1018, and an interface control circuit 1054. When system 1060 (as an example of system 960) is implemented in implantable stimulator 704 and external programming device 802, user interface 810 can be configured include user interface 1010, with presentation device 856 configured to be presentation device 1056, user input device 858 configured to be user input device 1058, and interface control circuit 854 configured to include interface control circuit 1054. In one embodiment, user interface 1010 can be implemented in a portable device suitable for use by the patient. The portable device can be a handheld device, such as a smart mobile device with an application installed to enable the device to be used as user interface 1010. Examples of such a portable device include a smartphone, a laptop computer, and a tablet computer.

Presentation device 1056 can display a graphical representation of electrode array(s) 909 and a graphical representation of the stimulation field. The stimulation field can be representation by a volume of activation and/or a distribution of stimulation energy over contact 906. For example, the stimulation field can be represented by the stimulation contacts being selected for delivering the neurostimulation or a fractionalization specifying a portion of the stimulation energy applied to each of contacts 906 (with stimulation contacts being the contacts for which the portion of the stimulation energy is not zero). In various embodiments, the stimulation field can be represented by a central point of stimulation (CPS). The CPS can be the center of the stimulation field that generally corresponds to the main cathode of fractionalized contacts in cathodic stimulation. User input device 1058 can receive user commands for moving the stimulation field. In various embodiments, presentation device 1056 can graphically show movement of the stimulation field in response to the user commands. When the stimulation field is represented by the CPS, user input device 1058 can receive commands for moving the CPS, and presentation device 1056 can show movement of the CPS in response to the user commands.

Interface control circuit 1054 can control operation of user interface 1010 and include a stimulation control circuit 1054. Stimulation control circuit 1020 can represent an example of stimulation control circuit 920 and can control the delivery of the neurostimulation using stimulation parameters. The stimulation parameters can specify the stimulation contacts, the sensing contacts, and an intensity of the neurostimulation, among other aspects of the neurostimulation. Stimulation control circuit 1020 includes a response detector 1062, a steering module 1064, and a mapping module 1066.

Response detector 1062 can represent an example of response detector 962 and can receive the sensed signal, detect one or more signal features from the sensed signal, and determine a response parameter using the detected one or more signal features. The response parameter is indicative of an intensity of the response to the neurostimulation. In one embodiment, the sensed signal is a neural signal including evoked compound action potentials (ECAPs) or evoked potential (EP), and the one or more signal features include one or more ECAP or EP features. Examples of the EP or ECAP features to be detected include:

N1: first negative peak in an evoked response that is correlated to the response of faster fibers such as Aβ fibers and myelinated fibers;

P2: second positive peak in the evoked response that is correlated with response of slower fibers;

N2 and P3: the second negative peak in the evoked response and the third positive peak in the evoked response, respectively, which are correlated with responses of even slower fibers (e.g., Aδ fibers); and A damped oscillation where N1, P1, N2, P2, N3, P3, and more successive damped peaks are observed in the positive and negative directions (ERNA: evoked resonant neural activity is a type of evoked response, observed in Subthalamic nucleus, Globus pallidum, and other brain structures). Examples of the response parameter determined using the detected one or more ECAP features include:

N1-to-P2 amplitude;
N1 to P2 curve length;
ECAP curve length (curve length over the duration of a complete ECAP response);
ECAP area under the curve (AUC, the area between the neural signal and a baseline over the ECAP curve length);
ECAP AUC with respect to a predefined constant value;
P2 peak delay, which is the time interval between a stimulus and the P2 of the evoked response to that stimulus;
presence of N2 and/or P3, and/or other extrema (maxima and minima) in the evoked response;
damping factor, frequency of the evoked oscillation, and/or variation or rate of variation of the evoked oscillation, if the evoked response exhibited multiple extrema (maxima and minima) attenuated over time (with damping);
variability (speed of change) of any of the above features with respect to the new spatial position;
rate of variability (acceleration of change) of any of the above features; and
any other morphological feature extracted from the evoked response.

In various embodiments, a stronger response (i.e., a response having a higher intensity) can be indicated by a greater magnitude and/or a different shape including, for example:

a greater N1-to-P2 amplitude;
a greater N1 to P2 curve length;
a greater ECAP curve length;
a greater ECAP AUC;
a greater ECAP AUC with respect to a predefined constant value a greater P2 peak delay;
a presence or greater presence of N2 and/or P3 and/or other extrema (maxima and minima) in the evoked response;
if the evoked response exhibited multiple extrema (maxima and minima) attenuated over time (with damping):
    a greater the damping factor,
    a greater the frequency of the evoked oscillation, and/or
    a greater the variation or rate of variation of the evoked oscillation;
a greater variability (speed of change) of any of the above features with respect to the new spatial position;
a greater rate of variability (acceleration of change) of any of the above features; and/or
a greater response in any other morphological feature from the evoked response.

In various embodiments in which SCS is applied, the response parameter used for indicating the intensity of response, and hence the paresthesia, can be derived from such characteristics of the evoked responses as seen on the sensed neural signal. In various embodiments, the response parameter can be used to indicate the patient's sensation of the neurostimulation (paresthesia or otherwise) and can be measured from the neural signal and/or a derivative of the neural signal. The response parameter can be used to indicate when the sensation is lost because the intensity of the stimulation is too low.

Mapping module 1066 can identify CSCs from contacts 906, identify BSCs from contacts 906 for each CSC of the identified CSCs, and map the identified CSCs to the identified BSCs. In various embodiments, mapping module 1066 can execute a mapping algorithm selecting stimulation contacts from the plurality of contacts, selecting sensing contacts from the plurality of contacts for each selected stimulation contact, determining the CSCs, and determining the BSCs for each of the CSCs. The mapping algorithm can occur prior to the actual steering to search for best pain-paresthesia overlap or during the actual steering. FIGS. 11 and 12 illustrate an embodiment of a process for mapping the CSCs to the BSCs. FIGS. 11 and 12 each illustrate two leads 1108A and 1108B parallelly placed over a portion of the spinal cord (in the portion of vertebrate shown). Leads 1108A and 1108B include electrode arrays 1109A and 1109B, respectively, each including 16 contacts. FIG. 11 shows, as an example, the stimulation field being moved with a different stimulation contact being selected each time (monopolar stimulation) and a different set of sensing contacts selected for the selected stimulation contact. In other examples, the stimulation can be delivered through more than one contact and using different polarities and different fractionalizations of the energy to each contact. The sensing contacts for each selected stimulation contact(s) are searched in the vicinity of the specific stimulation contact(s) used (as shown in FIG. 11). As the stimulation field moves, the stimulation contact moves, and for each stimulation contact, a search of candidates for best sensing contact(s) (BSC(s)) for that stimulation contact takes place. A guide for searching the BSC(s) for each stimulation contact can be based on using a distance from the selected stimulation contact or from the CPS or from the main cathode if multiple contacts fractionalized are used to stimulate. For example, a specified number of sensing contacts with the distances from the selected stimulation contact closest to a known optimal distance can be selected, or with distances within a range of distances (e.g., from 9 mm to 50 mm) from the selected stimulation contact. In the example as illustrated in FIG. 11, 4 contacts with distances from the selected stimulation contact closest to 20 millimeters are selected to be the sensing contacts for the selected stimulation contact, but the number of sensing contacts can be programmable or automatically selected by the algorithm.

In one embodiment, mapping module 1066 identifies the CSCs and BSCs automatically. The user selects or creates a field steering trajectory and starts the process (e.g., by entering a start command using user input device 1058), and the stimulation field is applied at the start location, moves, and provides the CSCs and BSCs as an outcome. At the start location, before the stimulation field moves to a different location, ECAP features are extracted from candidate BSC(s) in the vicinity of the stimulation contact. For each stimulation contact in the trajectory shown in FIG. 11 (trajectory: stimulation starts at top of right-side lead in the downward direction), the selection of the candidate BSC(s) entails a spatial search in the vicinity of each stimulation contact. The search can start at a specified distance range where all contacts meeting the distance range criteria (e.g., 9 mm<distance between main CSC cathode and sensing contact<50 min) are considered. For each of those sensing contacts considered, the ECAP is identified first, by progressively increasing the stimulation amplitude and storing the relationship of ECAP feature(s) versus stimulation amplitude (shown at the top of FIGS. 11 and 12 for each stimulation contact shown for FIG. 11, and stimulation contacts and CSC shown in FIG. 12). As the stimulation amplitude is increased, when the extracted ECAP features first indicate an ECAP is detected, the corresponding stimulation amplitude is considered to be the neural threshold (NT). The stimulation amplitude increase can continue until a value below the predicted discomfort threshold (DT), e.g., the maximum comfortable threshold, is reached. Optionally, the user can mark (e.g., using user input device 1058) when the patient stops feeling the stimulation, and/or mark when the patient starts feeling it or starts feeling discomfort. The ECAP feature(s) profiles for each stimulation contact can be stored for posterior comparison and decision of the BSCs and the CSCs. The ECAP features recorded for each candidate CSC are compared and those with the greater ECAP features are pre-selected as the candidate BSC or BSCs associated to the stimulation contact which is also a candidate CSC at this point. After the steering is completed through the spatial trajectory defined by the user, the ECAP feature(s) corresponding to each pre-selected candidate BSC for each stimulation contact explored (candidate CSC) in the trajectory, are compared, and those exceeding a specified threshold become the BSC(s) mapping to the stimulation contacts that become CSCs. The specified threshold applied to the BSCs to establish the CSC can be defined as a percentage below the maximum ECAP feature measured across all BSCs, or as the ECAP features exceeding a previously determined maximum tolerable threshold, or as the ECAP features exceeding a mathematical value computed from the recorded ECAP features from all candidate BSCs. Such mathematical value can be defined as the average across the 10% higher ECAP features from all candidate BSCs.

FIG. 12 shows the CSCs identified. CSCs can be the stimulation contacts that produce either (1) largest responses or largest increases in the evoked response sensed in their mapped BSCs when the stimulation field is moving, or (2) smallest responses or largest decreases in the evoked response when the stimulation field is moving.

In various embodiments, mapping the identified CSCs to the identified BSCs includes mapping stimulation parameters associated with each CSC of the identified CSCs to a profile of the BSCs identified for that CSC. The profile of the BSCs can include threshold parameters. Examples of such threshold parameters include:

a neural threshold (NT) being the minimum value of the response parameter corresponding to the minimum stimulation intensity at which the patient starts to feel the paresthesia; and a discomfort threshold (DT) being the value of the response parameter corresponding to the stimulation intensity at which the patient starts to feel discomfort.

The NT approximates the patient's perception threshold (PT), which is not used because the present system does not ask the patient for perception. An example for determining thresholds related to neurostimulation, including the NT and DT, is discussed in U.S. Provisional Patent Application No. 63/165,825, entitled "Automatic Calibration in an Implantable Stimulator Device Having Neural Sensing Capability", filed on Mar. 25, 2021, which is incorporated herein by reference in its entirety. In various embodiments, the threshold parameters can be determined manually or determined automatically as part of the mapping process using mapping module 1066.

Returning to FIG. 10, steering module 1064 can represent an example of steering module 964 and can execute a steering algorithm receiving commands for moving the stimulation field to any or each of the identified CSCs and to adjust the one or more parameters of the stimulation parameters for moving the stimulation field while keeping the intensity of the response to the neurostimulation substantially constant by maintaining a value of the response parameter between an upper threshold and a lower threshold. In one embodiment, steering module 1064 receives the response parameter from response detector 1062 in real time (i.e., during the steering) and adjusts the one or more parameters of the stimulation parameters using the received response parameter in real time. In another embodiment, steering module 1064 receives pre-stored data from storage device 1018 and to adjust the one or more parameters of the stimulation parameters using the received pre-stored data. The pre-stored data can include data produced by mapping module 1066 and stored in storage device 1018, such as a look-up table or another form of map that relates the stimulation parameters associated to each CSC to the profile of BSCs for that CSC. Steering module 1064 can adjust the upper threshold based on the DT and adjust the lower threshold based on NT, with the upper threshold being smaller than the DT and the lower threshold being larger than the NT. In one embodiment, steering module 1064 sets the upper threshold to aDT and sets the lower threshold to bNT, where a and b are programmable to allow adjustment depending on, for example, whether the user or the patient is to drive the steering. In one specific example, a is programmed to 0.5, and b is programmed to 1.1.

In various embodiments, steering module 1064 can steer the stimulation field by moving the CPS (as driven by the user or the patient) and receives values of the response parameter in real time. As the CPS is steered toward a CSC, sensing circuit 942 senses the signal, and response detector 1062 produces the response parameter, in real time, and steering module 1064 reduces the intensity of stimulation in response to the response parameter exceeding the upper threshold (e.g., 0.5DT). As the CPS is steered away from a CSC, sensing circuit 942 senses the signal, and response detector 1062 produces the response parameter, in real time, and steering module 1064 increases the intensity of stimulation in response to the response parameter falling below the lower threshold (e.g., 1.1NT).

In various other embodiments, steering module 1064 can steer the stimulation field by moving the CPS and using data pre-stored in storage device 1018. As the CPS is steered toward a CSC, steering module 1064 reduces the intensity of stimulation using pre-stored date relating the response parameter to the upper threshold (e.g., 0.5DT). As the CPS is steered away from a CSC, steering module 1064 increases the intensity of stimulation using pre-stored date relating the response parameter to the lower threshold (e.g., 1.1NT). The pre-store data can be produced by mapping module 1066 during a mapping process performed before the steering and stored in storage device 1018.

Figure 13:
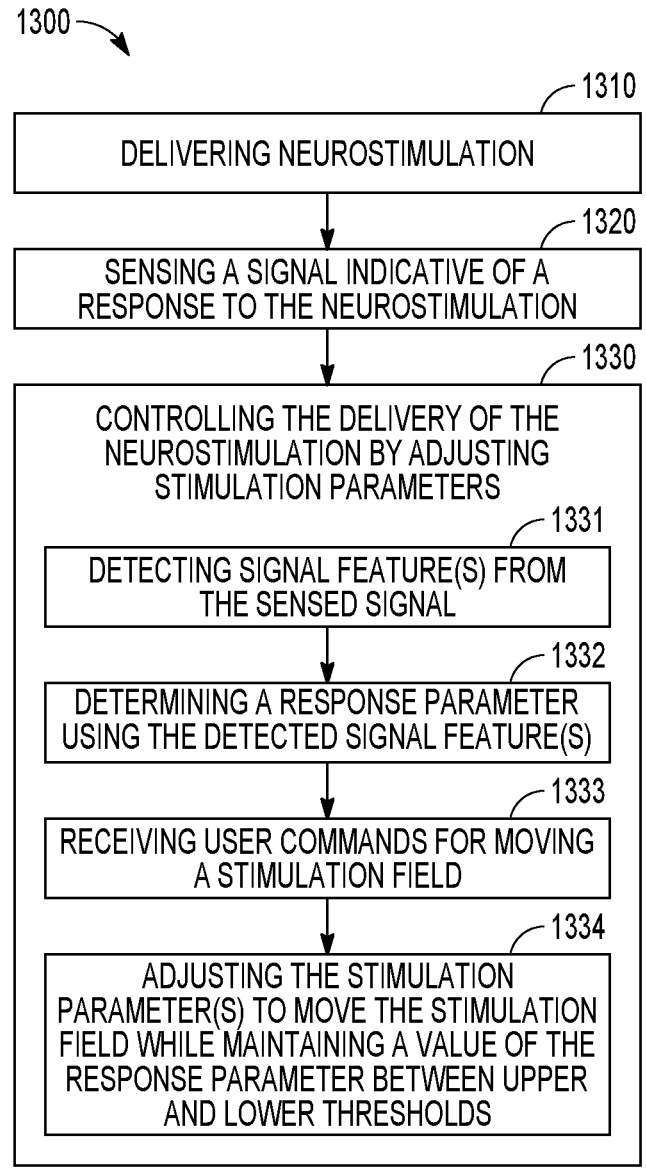
FIG. 13 illustrates an embodiment of a method for closed-loop steering of a stimulation field.

FIG. 13 illustrates an embodiment of a method 1300 for delivering neurostimulation to a patient, including closed-loop steering of a stimulation field of the neurostimulation for locating a sweet spot. In one embodiment, method 1300 is performed using system 960 or 970. In one embodiment, a non-transitory computer-readable storage medium includes instructions, which when executed by a system, such as system 960 or 970, cause the system to perform method 1300.

At 1310, the neurostimulation is delivered to a patient using one or more stimulation contacts selected from a plurality of contacts of one or more electrode arrays. In one embodiment, the one or more electrode arrays are incorporated into one or more implantable leads, and the neurostimulation is delivered from an implantable neurostimulator coupled to the one or more implantable leads. At 1320, a signal is sensed using one or more sensing contacts selected from the plurality of contacts. The signal is indicative of a response of the patient to the neurostimulation. In one embodiment, the signal is a neural signal including ECAPs. At 1330, the delivery of the neurostimulation is controlled by adjusting stimulation parameters using a processor, including performing steps 1331, 1332, 1333, and 1334.

At 1331, one or more signal features are detected from the sensed signal. In the embodiment in which the sensed signal is the neural signal including the ECAPs, one or more ECAP features are detected from the sensed signal.

At 1332, a response parameter is determined using the detected one or more signal features. The response parameter is indicative of an intensity of the response to the neurostimulation.

At 1333, user commands for moving a stimulation field is received. The stimulation field can be defined by a distribution of a stimulation energy of the neurostimulation over the plurality of contacts. In one embodiment, a graphical representation of the one or more electrode arrays and a graphical representation of the stimulation field are displayed on a display screen. The stimulation field is moved according to user commands for moving a CPS received using a user input device. The CPS is a center of the stimulation field. The movement of the stimulation field including the CPS is dynamically shown on the display screen as the CPS is being moved using the user input device. A mobile device providing for the display screen and the user input device, such as a smartphone with a touchscreen, is configured for use by the patient to enter the user commands for moving the stimulation field, so as to allow the patient to drive the steering for locating the sweet spot.

At 1334, one or more parameters of the stimulation parameters is adjusted to move the stimulation field according to the user commands while maintaining a value of the response parameter between an upper threshold and a lower threshold. In one embodiment, the upper threshold is adjusted based on a DT, and the lower threshold is adjusted based on a NT. The DT is the value of the response parameter corresponding to the stimulation intensity at which the patient starts to feel discomfort resulting from the neurostimulation. The NT is the minimum value of the response parameter corresponding to the minimum stimulation intensity at which the patient starts to feel the neurostimulation. In one embodiment, the upper threshold is set to aDT, and the lower threshold is set to bNT, where a and b having programmable values.

Figure 14:
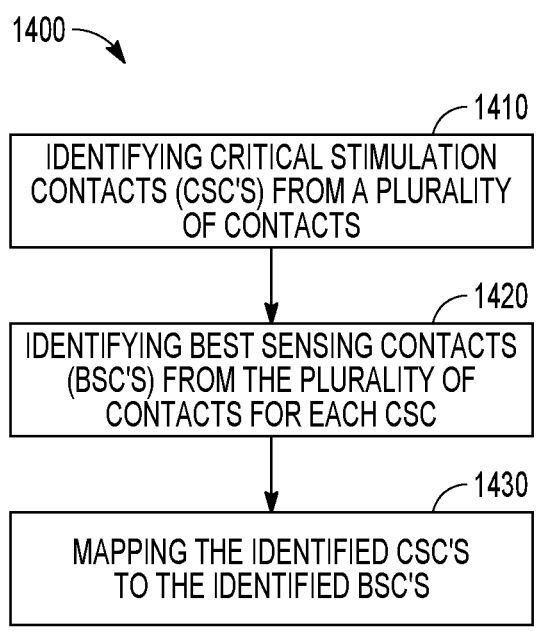
FIG. 14 illustrates an embodiment of a method for mapping CSCs to BSCs.

FIG. 14 illustrates an embodiment of a method 1400 for mapping CSCs to BSCs. In one embodiment, method 1400 is performed using system 970. In one embodiment, a non-transitory computer-readable storage medium includes instructions, which when executed by a system, such as system 970, cause the system to perform method 1400, such as by executing a mapping algorithm using a processor of the system. In various embodiments, methods 1300 and 1400 are performed using a processor of the system, such as system 970, with method 1400 being performed first to prepare data and identify CSCs and BSCs in preparation for performing method 1300.

At 1410, CSCs are identified from the plurality of contacts. The CSCs are stimulation contacts associated with the most significant response to the neurostimulation when being used to deliver the neurostimulation. In one embodiment, CSCs are identified as the stimulation contacts that show either (1) largest responses or largest increases in the response when the stimulation field is moving, or (2) smallest responses or largest decreases in the response when the stimulation field is moving. In another embodiment, CSCs are identified as the stimulation contacts with the lowest NT or the stimulation contacts with the lowest DT.

At 1420, BSCs are identified from the plurality of contacts for each CSC of the identified CSCs. BSCs are sensing contacts associated with the sensed signal showing the largest amplitude of the response to the neurostimulation.

At 1430, the identified CSCs are mapped to the identified BSCs. This includes mapping the stimulation parameters associated with each CSC of the identified CSCs to threshold parameters (e.g., the DT and the NT) associated with the BSCs identified for that CSC.

In one embodiment, after the CSCs and the BSCs are identified, method 1300 is performed in real time. The response parameter is determined in real time. The one or more parameters of the stimulation parameters are adjusted to reduce the intensity of stimulation in response to the response parameter exceeding the upper threshold while the stimulation field is moving toward each CSC of the identified CSCs and adjusted to increase the intensity of stimulation in response to the response parameter falling below the lower threshold while the stimulation field is moving away from the each CSC.

In another embodiment, after the CSCs and the BSCs are identified, method 1300 is performed using pre-stored data, such as data resulting from a performance of method 1400. Predetermined values for the response parameter associated with the identified BSCs are stored. The one or more parameters of the stimulation parameters are adjusted to reduce the intensity of stimulation using the predetermined values for the response parameter while the stimulation field is moving toward each CSC of the identified CSCs and adjusted to increase the intensity of stimulation using the predetermined values for the response parameter while the stimulation field is moving away from the each CSC.

It is to be understood that the above detailed description is intended to be illustrative, and not restrictive. Other embodiments will be apparent to those of skill in the art upon reading and understanding the above description. The scope of the invention should, therefore, be determined with reference to the appended claims, along with the full scope of equivalents to which such claims are entitled.

What is claimed is:

1. A system for delivering neurostimulation to a patient using one or more electrode arrays including a plurality of contacts, the system comprising:
   a stimulation output circuit configured to deliver the neurostimulation using one or more stimulation contacts selected from the plurality of contacts;
   a sensing circuit configured to sense a signal using one or more sensing contacts selected from the plurality of contacts, the signal indicative of a response to the neurostimulation; and
   a stimulation control circuit configured to control the delivery of the neurostimulation using stimulation parameters, the stimulation control circuit including:
      a response detector configured to detect one or more signal features from the sensed signal and to determine a response parameter using the detected one or more signal features, the response parameter indicative of an intensity of the response to the neurostimulation; and
      a steering module configured to receive user commands for moving a stimulation field defined by a distribution of a stimulation energy of the neurostimulation over the plurality of contacts and to adjust one or more parameters of the stimulation parameters to move the stimulation field according to the user commands and to adjust an intensity of the neurostimulation to maintain a value of the response parameter between an upper threshold and a lower threshold while the stimulation field is being moved according to the user commands.

2. The system of claim 1, wherein the sensing circuit is configured to sense a neural signal including evoked potentials, and the response detector is configured to detect one or more evoked potential features from the sensed signal and to determine a response parameter using the detected one or more evoked potential features.

3. The system of claim 1, wherein the stimulation control circuit further comprises a mapping module configured to identify critical stimulation contacts (CSCs) from the plurality of contacts, the CSCs each being a stimulation contact of the stimulation contacts that is associated with overstimulation or understimulation, to identify best sensing contacts (BSCs) from the plurality of contacts for each CSC of the identified CSCs, and to map the identified CSCs to the identified BSCs.

4. The system of claim 3, wherein the mapping module is configured to execute a mapping algorithm selecting stimulation contacts from the plurality of contacts, selecting sensing contacts from the plurality of contacts for each selected stimulation contact, determining the CSCs from the selected stimulation contacts, determining the BSCs for each of the CSCs from the selected sensing contacts, and mapping the stimulation parameters associated with each CSC of the identified CSCs to threshold parameters associated with the BSCs identified for that CSC.

5. The system of claim 3, wherein the steering module is configured to receive the response parameter from the response detector in real time and to adjust the one or more parameters of the stimulation parameters using the received response parameter.

6. The system of claim 5, wherein the steering module is configured to:
   adjust the one or more parameters of the stimulation parameters to reduce the intensity of the neurostimulation in response to the response parameter exceeding the upper threshold while the stimulation field is moving toward each CSC of the identified CSCs; and
   adjust the one or more parameters of the stimulation parameters to increase the intensity of the neurostimulation in response to the response parameter falling below the lower threshold while the stimulation field is moving away from each CSC of the identified CSCs.

7. The system of claim 3, further comprising a storage device storing predetermined values for the response parameter associated with the identified BSCs, and wherein the steering module is configured to adjust the one or more parameters of the stimulation parameters using the predetermined values for the response parameter.

8. The system of claim 3, wherein the steering module is configured to adjust the upper threshold based on a discomfort threshold (DT) of the threshold parameters and to adjust the lower threshold based on a neural threshold (NT) of the threshold parameters, the DT being a value of the response parameter corresponding to a stimulation intensity at which the patient starts to feel discomfort resulting from the neurostimulation, the NT being a minimum value of the response parameter corresponding to a minimum stimulation intensity at which the patient starts to feel the neurostimulation.

9. The system of claim 1, further comprising a user interface including:
   a presentation device configured to display a graphical representation of the one or more electrode arrays and a graphical representation of the stimulation field including a central point of stimulation (CPS) being a center of the stimulation field; and a user input device configured to receive the user commands for moving the stimulation field by moving the CPS.

10. The system of claim 9, comprising a smartphone configured for use by the patient and including the user interface.

11. A method for delivering neurostimulation to a patient, the method comprising:
  delivering the neurostimulation using one or more stimulation contacts selected from a plurality of contacts of one or more electrode arrays;
  sensing a signal using one or more sensing contacts selected from the plurality of contacts, the signal indicative of a response to the neurostimulation;
  controlling the delivery of the neurostimulation by adjusting stimulation parameters using a processor, including:
  detecting one or more signal features from the sensed signal;
  determining a response parameter using the detected one or more signal features, the response parameter indicative of an intensity of the response to the neurostimulation;
  receiving user commands for moving a stimulation field defined by a distribution of a stimulation energy of the neurostimulation over the plurality of contacts; adjusting one or more parameters of the stimulation parameters to move the stimulation field according to the user commands; and
  adjusting an intensity of the neurostimulation to maintain a value of the response parameter between an upper threshold and a lower threshold while the stimulation field is being moved according to the user commands.

12. The method of claim 11, wherein sensing the signal comprises sensing a neural signal including evoked potentials, and detecting the one or more signal features comprises detecting one or more evoked potential features from the sensed signal.

13. The method of claim 11, further comprising executing a mapping algorithm using the processor, including:
  identifying critical stimulation contacts (CSCs) from the plurality of contacts, the CSCs each being a stimulation contact of the stimulation contacts that is associated with overstimulation or understimulation;
  identifying best sensing contacts (BSCs) from the plurality of contacts for each CSC of the identified CSCs; and
  mapping the identified CSCs and to the identified BSCs, including mapping the stimulation parameters associated with each CSC of the identified CSCs to threshold parameters associated with the BSCs identified for that CSC.

14. The method of claim 13, wherein adjusting the one or more parameters of the stimulation parameters comprises:
  receiving the response parameter in real time;
  adjusting the one or more parameters of the stimulation parameters to reduce the intensity of the neurostimulation in response to the response parameter received in real time exceeding the upper threshold while the stimulation field is moving toward each CSC of the identified CSCs; and
  adjusting the one or more parameter of the stimulation parameters to increase the intensity of the neurostimulation in response to the response parameter received in real time falling below the lower threshold while the stimulation field is moving away from the each CSC.

15. The method of claim 13, wherein adjusting the one or more parameters of the stimulation parameters comprises:
  storing predetermined values for the response parameter associated with the identified BSCs;
  adjusting the one or more parameters of the stimulation parameters to reduce the intensity of the neurostimulation using the predetermined values for the response parameter while the stimulation field is moving toward each CSC of the identified CSCs; and
  adjusting the one or more parameter of the stimulation parameters to increase the intensity of the neurostimulation using the predetermined values for the response parameter while the stimulation field is moving away from the each CSC.

16. The method of claim 13, further comprising:
  adjusting the upper threshold based on a discomfort threshold (DT) of the threshold parameters, the DT being a value of the response parameter corresponding to a stimulation intensity at which the patient starts to feel discomfort resulting from the neurostimulation; and
  adjusting the lower threshold based on a neural threshold (NT) of the threshold parameters, the NT being a minimum value of the response parameter corresponding to a minimum stimulation intensity at which the patient starts to feel the neurostimulation.

17. The method of claim 16, further comprising:
  receiving programmable values a and b;
  setting the upper threshold to aDT; and
  setting the lower threshold to bNT.

18. The method of claim 11, further comprising:
  displaying a graphical representation of the one or more electrode arrays and a graphical representation of the stimulation field on a display screen;
  receiving the user commands for moving the stimulation field by moving a central point of stimulation (CPS) using a user input device, the CPS being a center of the stimulation field; and
  graphically showing movement of the stimulation field including the CPS on the display screen as the CPS is being moved.

19. The method of claim 18, further comprising configuring a mobile device for use by the patient to enter the user commands for moving the stimulation field.

20. A non-transitory computer-readable storage medium including instructions, which when executed by a system, cause the system to perform a method for delivering neurostimulation to a patient, the method comprising:
  delivering the neurostimulation using one or more stimulation contacts selected from a plurality of contacts of one or more electrode arrays;
  sensing a signal using one or more sensing contacts selected from the plurality of contacts, the signal indicative of a response to the neurostimulation;
  controlling the delivery of the neurostimulation by adjusting stimulation parameters using a processor, including:
    detecting one or more signal features from the sensed signal;
    determining a response parameter using the detected one or more signal features, the response parameter indicative of an intensity of the response to the neurostimulation;
  receiving user commands for moving a stimulation field defined by a distribution of a stimulation energy of the neurostimulation over the plurality of contacts;
  adjusting one or more parameters of the stimulation parameters to move the stimulation field according to the user commands; and adjusting an intensity of the neurostimulation to maintain a value of the response parameter between an upper threshold and a lower threshold while the stimulation field is being moved according to the user commands.

* * * * *